(12) United States Patent
Haug et al.

(10) Patent No.: US 9,241,968 B2
(45) Date of Patent: Jan. 26, 2016

(54) NONAPEPTIDE WITH ANTI-TUMOUR ACTIVITY

(75) Inventors: Bengt Erik Haug, Tertnes (NO); Jon Amund Eriksen, Porsgrunn (NO); John Sigurd Svendsen, Kvaloysletta (NO); Oystein Rekdal, Hvalstad (NO)

(73) Assignee: Lytix Biopharma AS, Tromso (NO)

( * ) Notice: Subject to any disclaimer, the term of this patent is extended or adjusted under 35 U.S.C. 154(b) by 941 days.

(21) Appl. No.: 13/131,045

(22) PCT Filed: Sep. 11, 2009

(86) PCT No.: PCT/EP2009/006744
§ 371 (c)(1),
(2), (4) Date: Sep. 9, 2011

(87) PCT Pub. No.: WO2010/060497
PCT Pub. Date: Jun. 3, 2010

(65) Prior Publication Data
US 2011/0318364 A1   Dec. 29, 2011

(30) Foreign Application Priority Data
Nov. 26, 2008   (GB) .................................. 0821616.0

(51) Int. Cl.
| | | |
|---|---|---|
| *A61P 31/12* | (2006.01) | |
| *A61K 38/08* | (2006.01) | |
| *C07K 7/06* | (2006.01) | |

(52) U.S. Cl.
CPC .. *A61K 38/08* (2013.01); *C07K 7/06* (2013.01)

(58) Field of Classification Search
CPC ........... A61K 38/00; C07K 7/06; C07K 14/47
See application file for complete search history.

(56) References Cited

U.S. PATENT DOCUMENTS

| | | | |
|---|---|---|---|
| 6,677,116 | B1 | 1/2004 | Blaschuk et al. |
| 2008/0019993 | A1* | 1/2008 | Eliassen et al. ............ 424/185.1 |

FOREIGN PATENT DOCUMENTS

| | | |
|---|---|---|
| WO | 92/14756 A1 | 9/1992 |
| WO | 99/58552 A2 | 11/1999 |
| WO | 99/58564 A1 | 11/1999 |
| WO | 00/02581 A1 | 1/2000 |
| WO | 00/12542 A2 | 3/2000 |
| WO | 00/66153 A1 | 11/2000 |
| WO | 01/19852 A2 | 3/2001 |
| WO | 0166147 A2 | 9/2001 |
| WO | 02/051994 A2 | 7/2002 |
| WO | 02/070679 A2 | 9/2002 |
| WO | 02/094312 A1 | 11/2002 |
| WO | 2007107748 A2 | 9/2007 |
| WO | WO 2007107748 A2 * | 9/2007 |
| WO | 2008/022444 A1 | 2/2008 |
| WO | WO 2008022444 A1 * | 2/2008 ............... C07K 7/06 |

OTHER PUBLICATIONS

Waterbeemd et al. (Lipophilicity of amino acids, Amino Acids, vol. 7:129-145 (1994).*

(Continued)

*Primary Examiner* — James H Alstrum Acevedo
*Assistant Examiner* — Randall L Beane
(74) *Attorney, Agent, or Firm* — Fox Rothschild LLP

(57) ABSTRACT

The present invention relates to peptides or peptide like molecules and their uses in therapy, in particular as anti-tumor agents.

13 Claims, 4 Drawing Sheets

(56) References Cited

OTHER PUBLICATIONS

Figure 1:
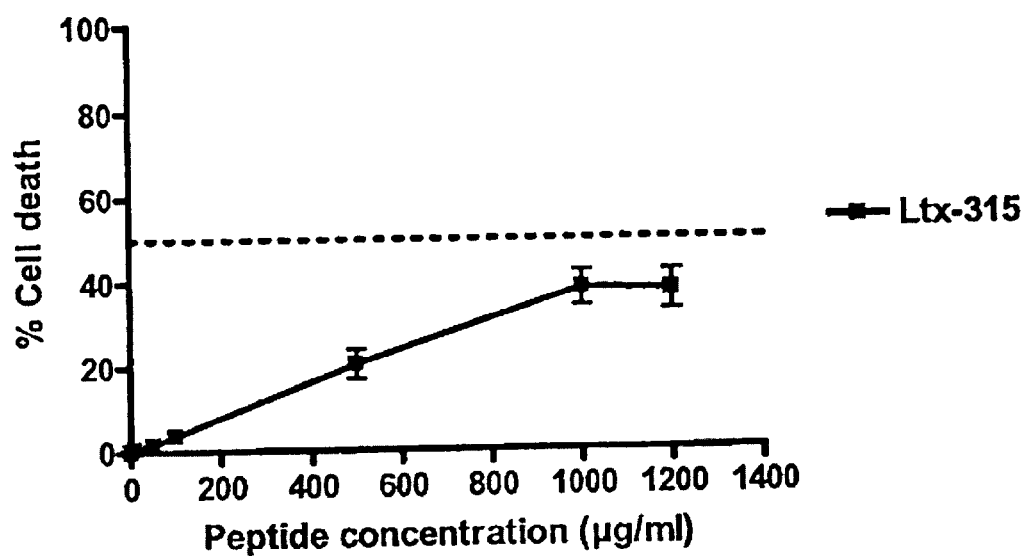

Eliassen, et al. "Enhanced Antitumour Activity of 15-Residue Bovine Lactoferricin Derivatives and Lipophillic N-Terminal Modifications." Journal of Peptide Science 9: 510-517. Jan. 2003.
Giuliani et al, (2007) Antimicrobial peptides: an overview of a promising class of therapeutics. CEJB 2: 1-33.
Hicks et al, (2007) De Novo Design of Selective Antibiotic Peptides by Incorporation of Unnatural Amino Acids. J. Med. Chem. 50: 3026-36.
Yang et al, (2004), The effects of shortening lactoferrin derived peptide against tumour cells, bacteria and normal human cells. J Peptide Sci. 10: 37-46.
Lingnau et al. IC31 and IC30, novel types of vaccine adjuvant based on peptide delivery systems. Expert Rev. Vaccines 6(5), pp. 741-746. (2007).
Brooks et al. Cell-penetrating peptides: Application in vaccine delivery. Biochemica et Biophysica Acta 1805, pp. 25-34. (2010).

* cited by examiner

Figure 4

Figure 5

SEQUENCE LISTING

```
<160> NUMBER OF SEQ ID NOS: 42

<210> SEQ ID NO 1
<211> LENGTH: 9
<212> TYPE: PRT
<213> ORGANISM: artificial
<220> FEATURE:
<223> OTHER INFORMATION: Synthetic sequence
<220> FEATURE:
<221> NAME/KEY: MISC_FEATURE
<222> LOCATION: (1)..(2)
<223> OTHER INFORMATION: Cationic amino acid
<220> FEATURE:
<221> NAME/KEY: MISC_FEATURE
<222> LOCATION: (3)..(4)
<223> OTHER INFORMATION: Lipophilic amino acid
<220> FEATURE:
<221> NAME/KEY: MISC_FEATURE
<222> LOCATION: (5)..(6)
<223> OTHER INFORMATION: Cationic amino acid
<220> FEATURE:
<221> NAME/KEY: MISC_FEATURE
<222> LOCATION: (7)..(8)
<223> OTHER INFORMATION: Lipophilic amino acid
```

```
<220> FEATURE:
<221> NAME/KEY: MISC_FEATURE
<222> LOCATION: (9)..(9)
<223> OTHER INFORMATION: Cationic amino acid

<400> SEQUENCE: 1

Xaa Xaa Xaa Xaa Xaa Xaa Xaa Xaa Xaa
1               5

<210> SEQ ID NO 2
<211> LENGTH: 9
<212> TYPE: PRT
<213> ORGANISM: artificial
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Lipophilic amino acid
<220> FEATURE:
<221> NAME/KEY: MISC_FEATURE
<222> LOCATION: (2)..(3)
<223> OTHER INFORMATION: Cationic amino acid
<220> FEATURE:
<221> NAME/KEY: MISC_FEATURE
<222> LOCATION: (4)..(5)
<223> OTHER INFORMATION: Lipophilic amino acid
<220> FEATURE:
<221> NAME/KEY: MISC_FEATURE
<222> LOCATION: (6)..(7)
<223> OTHER INFORMATION: Cationic amino acid
<220> FEATURE:
<221> NAME/KEY: MISC_FEATURE
<222> LOCATION: (8)..(8)
<223> OTHER INFORMATION: Lipophilic amino acid
<220> FEATURE:
<221> NAME/KEY: MISC_FEATURE
<222> LOCATION: (9)..(9)
<223> OTHER INFORMATION: Cationic amino acid

<400> SEQUENCE: 2

Xaa Xaa Xaa Xaa Xaa Xaa Xaa Xaa Xaa
1               5

<210> SEQ ID NO 3
<211> LENGTH: 9
<212> TYPE: PRT
<213> ORGANISM: artificial
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Cationic amino acid
<220> FEATURE:
<221> NAME/KEY: MISC_FEATURE
<222> LOCATION: (2)..(3)
<223> OTHER INFORMATION: Lipophilic amino acid
<220> FEATURE:
<221> NAME/KEY: MISC_FEATURE
<222> LOCATION: (4)..(5)
<223> OTHER INFORMATION: Cationic amino acid
<220> FEATURE:
<221> NAME/KEY: MISC_FEATURE
<222> LOCATION: (6)..(7)
<223> OTHER INFORMATION: Lipophilic amino acid
<220> FEATURE:
<221> NAME/KEY: MISC_FEATURE
<222> LOCATION: (8)..(9)
<223> OTHER INFORMATION: Cationic amino acid

<400> SEQUENCE: 3

Xaa Xaa Xaa Xaa Xaa Xaa Xaa Xaa Xaa
1               5
```

-continued

```
<210> SEQ ID NO 4
<211> LENGTH: 9
<212> TYPE: PRT
<213> ORGANISM: artificial
<220> FEATURE:
<223> OTHER INFORMATION: Synthetic sequence
<220> FEATURE:
<221> NAME/KEY: MISC_FEATURE
<222> LOCATION: (1)..(2)
<223> OTHER INFORMATION: Cationic amino acid
<220> FEATURE:
<221> NAME/KEY: MISC_FEATURE
<222> LOCATION: (3)..(4)
<223> OTHER INFORMATION: Lipophilic amino acid
<220> FEATURE:
<221> NAME/KEY: MISC_FEATURE
<222> LOCATION: (5)..(5)
<223> OTHER INFORMATION: Cationic amino acid
<220> FEATURE:
<221> NAME/KEY: MISC_FEATURE
<222> LOCATION: (6)..(7)
<223> OTHER INFORMATION: Lipophilic amino acid
<220> FEATURE:
<221> NAME/KEY: MISC_FEATURE
<222> LOCATION: (8)..(9)
<223> OTHER INFORMATION: Cationic amino acid

<400> SEQUENCE: 4

Xaa Xaa Xaa Xaa Xaa Xaa Xaa Xaa Xaa
1               5

<210> SEQ ID NO 5
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Cationic amino acid
<220> FEATURE:
<221> NAME/KEY: MISC_FEATURE
<222> LOCATION: (2)..(2)
<223> OTHER INFORMATION: Lipophilic amino acid
<220> FEATURE:
<221> NAME/KEY: MISC_FEATURE
<222> LOCATION: (3)..(4)
<223> OTHER INFORMATION: Cationic amino acid
<220> FEATURE:
<221> NAME/KEY: MISC_FEATURE
<222> LOCATION: (5)..(6)
<223> OTHER INFORMATION: Lipophilic amino acid
<220> FEATURE:
<221> NAME/KEY: MISC_FEATURE
<222> LOCATION: (7)..(8)
<223> OTHER INFORMATION: Cationic amino acid
<220> FEATURE:
<221> NAME/KEY: MISC_FEATURE
<222> LOCATION: (9)..(9)
<223> OTHER INFORMATION: Lipophilic amino acid

<400> SEQUENCE: 5

Xaa Xaa Xaa Xaa Xaa Xaa Xaa Xaa Xaa
1               5

<210> SEQ ID NO 6
<211> LENGTH: 9
<212> TYPE: PRT
<213> ORGANISM: Artificial
<220> FEATURE:
<223> OTHER INFORMATION: Synthetic sequence
```

```
<220> FEATURE:
<221> NAME/KEY: MISC_FEATURE
<222> LOCATION: (1)..(2)
<223> OTHER INFORMATION: Cationic amino acid
<220> FEATURE:
<221> NAME/KEY: MISC_FEATURE
<222> LOCATION: (3)..(3)
<223> OTHER INFORMATION: Non genetically coded lipophilic amino acid
<220> FEATURE:
<221> NAME/KEY: MISC_FEATURE
<222> LOCATION: (4)..(4)
<223> OTHER INFORMATION: Lipophilic amino acid
<220> FEATURE:
<221> NAME/KEY: MISC_FEATURE
<222> LOCATION: (5)..(6)
<223> OTHER INFORMATION: Cationic amino acid
<220> FEATURE:
<221> NAME/KEY: MISC_FEATURE
<222> LOCATION: (7)..(8)
<223> OTHER INFORMATION: Lipophilic amino acid
<220> FEATURE:
<221> NAME/KEY: MISC_FEATURE
<222> LOCATION: (9)..(9)
<223> OTHER INFORMATION: Cationic amino acid

<400> SEQUENCE: 6

Xaa Xaa Xaa Xaa Xaa Xaa Xaa Xaa Xaa
1               5

<210> SEQ ID NO 7
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(2)
<223> OTHER INFORMATION: Cationic amino acid
<220> FEATURE:
<221> NAME/KEY: MISC_FEATURE
<222> LOCATION: (3)..(4)
<223> OTHER INFORMATION: Lipophilic amino acid
<220> FEATURE:
<221> NAME/KEY: MISC_FEATURE
<222> LOCATION: (5)..(6)
<223> OTHER INFORMATION: Cationic amino acid
<220> FEATURE:
<221> NAME/KEY: MISC_FEATURE
<222> LOCATION: (7)..(7)
<223> OTHER INFORMATION: Lipophilic amino acid
<220> FEATURE:
<221> NAME/KEY: MISC_FEATURE
<222> LOCATION: (8)..(8)
<223> OTHER INFORMATION: Non genetically coded lipophilic amino acid
<220> FEATURE:
<221> NAME/KEY: MISC_FEATURE
<222> LOCATION: (9)..(9)
<223> OTHER INFORMATION: Cationic amino acid

<400> SEQUENCE: 7

Xaa Xaa Xaa Xaa Xaa Xaa Xaa Xaa Xaa
1               5

<210> SEQ ID NO 8
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(2)
<223> OTHER INFORMATION: Cationic amino acid
```

```
<220> FEATURE:
<221> NAME/KEY: MISC_FEATURE
<222> LOCATION: (3)..(3)
<223> OTHER INFORMATION: Lipophilic amino acid
<220> FEATURE:
<221> NAME/KEY: MISC_FEATURE
<222> LOCATION: (4)..(4)
<223> OTHER INFORMATION: Non genetically coded lipophilic amino acid
<220> FEATURE:
<221> NAME/KEY: MISC_FEATURE
<222> LOCATION: (5)..(6)
<223> OTHER INFORMATION: Cationic amino acid
<220> FEATURE:
<221> NAME/KEY: MISC_FEATURE
<222> LOCATION: (7)..(8)
<223> OTHER INFORMATION: Lipophilic amino acid
<220> FEATURE:
<221> NAME/KEY: MISC_FEATURE
<222> LOCATION: (9)..(9)
<223> OTHER INFORMATION: Cationic amino acid

<400> SEQUENCE: 8

Xaa Xaa Xaa Xaa Xaa Xaa Xaa Xaa Xaa
1               5

<210> SEQ ID NO 9
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Lipophilic amino acid
<220> FEATURE:
<221> NAME/KEY: MISC_FEATURE
<222> LOCATION: (2)..(3)
<223> OTHER INFORMATION: Cationic amino acid
<220> FEATURE:
<221> NAME/KEY: MISC_FEATURE
<222> LOCATION: (4)..(4)
<223> OTHER INFORMATION: Lipophilic amino acid
<220> FEATURE:
<221> NAME/KEY: MISC_FEATURE
<222> LOCATION: (5)..(5)
<223> OTHER INFORMATION: Non genetically coded lipophilic amino acid
<220> FEATURE:
<221> NAME/KEY: MISC_FEATURE
<222> LOCATION: (6)..(7)
<223> OTHER INFORMATION: Cationic amino acid
<220> FEATURE:
<221> NAME/KEY: MISC_FEATURE
<222> LOCATION: (8)..(8)
<223> OTHER INFORMATION: Lipophilic amino acid
<220> FEATURE:
<221> NAME/KEY: MISC_FEATURE
<222> LOCATION: (9)..(9)
<223> OTHER INFORMATION: Cationic amino acid

<400> SEQUENCE: 9

Xaa Xaa Xaa Xaa Xaa Xaa Xaa Xaa Xaa
1               5

<210> SEQ ID NO 10
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Diphenylalanine
```

```
<400> SEQUENCE: 10

Xaa Lys Lys Trp Trp Lys Lys Trp Lys
1               5

<210> SEQ ID NO 11
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (5)..(5)
<223> OTHER INFORMATION: diphenylalanine

<400> SEQUENCE: 11

Trp Lys Lys Trp Xaa Lys Lys Trp Lys
1               5

<210> SEQ ID NO 12
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (8)..(8)
<223> OTHER INFORMATION: diphenylalanine

<400> SEQUENCE: 12

Trp Lys Lys Trp Trp Lys Lys Xaa Lys
1               5

<210> SEQ ID NO 13
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: biphenylalanine

<400> SEQUENCE: 13

Xaa Lys Lys Trp Trp Lys Lys Trp Lys
1               5

<210> SEQ ID NO 14
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: biphenylalanine

<400> SEQUENCE: 14

Trp Lys Lys Xaa Trp Lys Lys Trp Lys
1               5

<210> SEQ ID NO 15
<211> LENGTH: 9
<212> TYPE: PRT
<213> ORGANISM: Artificial
```

```
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: D-amino acids
<220> FEATURE:
<221> NAME/KEY: MISC_FEATURE
<222> LOCATION: (5)..(5)
<223> OTHER INFORMATION: diphenylalanine

<400> SEQUENCE: 15

Trp Lys Lys Trp Xaa Lys Lys Trp Lys
1               5

<210> SEQ ID NO 16
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: diphenylalanine

<400> SEQUENCE: 16

Lys Lys Trp Xaa Lys Lys Trp Trp Lys
1               5

<210> SEQ ID NO 17
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (4)..(4)
<223> OTHER INFORMATION: diphenylalanine
<220> FEATURE:
<221> NAME/KEY: MISC_FEATURE
<222> LOCATION: (5)..(6)
<223> OTHER INFORMATION: D-amino acid
<220> FEATURE:
<221> NAME/KEY: MISC_FEATURE
<222> LOCATION: (9)..(9)
<223> OTHER INFORMATION: D-amino acid

<400> SEQUENCE: 17

Lys Lys Trp Xaa Lys Lys Trp Trp Lys
1               5

<210> SEQ ID NO 18
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: diphenylalanine
<220> FEATURE:
<221> NAME/KEY: MISC_FEATURE
<222> LOCATION: (8)..(8)
<223> OTHER INFORMATION: diphenylalanine
```

```
<400> SEQUENCE: 18

Lys Lys Trp Xaa Lys Lys Trp Xaa Lys
1               5

<210> SEQ ID NO 19
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: biphenylalanine

<400> SEQUENCE: 19

Lys Lys Trp Xaa Lys Lys Trp Trp Lys
1               5

<210> SEQ ID NO 20
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (2)..(2)
<223> OTHER INFORMATION: biphenylalanine

<400> SEQUENCE: 20

Lys Xaa Lys Lys Trp Trp Lys Lys Trp
1               5

<210> SEQ ID NO 21
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: biphenylalanine

<400> SEQUENCE: 21

Lys Lys Xaa Trp Lys Lys Trp Trp Lys
1               5

<210> SEQ ID NO 22
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (7)..(7)
<223> OTHER INFORMATION: diphenylalanine

<400> SEQUENCE: 22

Lys Lys Trp Trp Lys Lys Xaa Trp Lys
1               5

<210> SEQ ID NO 23
<211> LENGTH: 9
<212> TYPE: PRT
<213> ORGANISM: Artificial
```

```
<220> FEATURE:
<223> OTHER INFORMATION: Synthetic sequence
<220> FEATURE:
<221> NAME/KEY: MISC_FEATURE
<222> LOCATION: (8)..(8)
<223> OTHER INFORMATION: diphenylalanine

<400> SEQUENCE: 23

Lys Lys Trp Trp Lys Lys Trp Xaa Lys
1               5

<210> SEQ ID NO 24
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: diphenylalanine

<400> SEQUENCE: 24

Lys Trp Xaa Lys Lys Trp Trp Lys Lys
1               5

<210> SEQ ID NO 25
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (7)..(7)
<223> OTHER INFORMATION: diphenylalanine

<400> SEQUENCE: 25

Lys Lys Trp Trp Lys Trp Xaa Lys Lys
1               5

<210> SEQ ID NO 26
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(2)
<223> OTHER INFORMATION: Orn
<220> FEATURE:
<221> NAME/KEY: MISC_FEATURE
<222> LOCATION: (4)..(4)
<223> OTHER INFORMATION: diphenylalanine
<220> FEATURE:
<221> NAME/KEY: MISC_FEATURE
<222> LOCATION: (5)..(6)
<223> OTHER INFORMATION: Orn
<220> FEATURE:
<221> NAME/KEY: MISC_FEATURE
<222> LOCATION: (9)..(9)
<223> OTHER INFORMATION: Orn

<400> SEQUENCE: 26

Xaa Xaa Trp Xaa Xaa Xaa Trp Trp Xaa
1               5
```

```
<210> SEQ ID NO 27
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(2)
<223> OTHER INFORMATION: Dpr
<220> FEATURE:
<221> NAME/KEY: MISC_FEATURE
<222> LOCATION: (4)..(4)
<223> OTHER INFORMATION: diphenylalanine
<220> FEATURE:
<221> NAME/KEY: MISC_FEATURE
<222> LOCATION: (5)..(6)
<223> OTHER INFORMATION: Dpr
<220> FEATURE:
<221> NAME/KEY: MISC_FEATURE
<222> LOCATION: (9)..(9)
<223> OTHER INFORMATION: Dpr

<400> SEQUENCE: 27

Xaa Xaa Trp Xaa Xaa Xaa Trp Trp Xaa
1               5

<210> SEQ ID NO 28
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: diphenylalanine

<400> SEQUENCE: 28

Arg Arg Trp Xaa Arg Arg Trp Trp Arg
1               5

<210> SEQ ID NO 29
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (6)..(6)
<223> OTHER INFORMATION: diphenylalanine

<400> SEQUENCE: 29

Lys Trp Trp Lys Lys Xaa Trp Lys Lys
1               5

<210> SEQ ID NO 30
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (2)..(2)
<223> OTHER INFORMATION: diphenylalanine

<400> SEQUENCE: 30

Lys Xaa Lys Lys Trp Trp Lys Lys Trp
1               5
```

-continued

```
<210> SEQ ID NO 31
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: diphenylalanine

<400> SEQUENCE: 31

Lys Lys Xaa Trp Lys Lys Trp Trp Lys
1               5

<210> SEQ ID NO 32
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: D-amino acid
<220> FEATURE:
<221> NAME/KEY: MISC_FEATURE
<222> LOCATION: (6)..(6)
<223> OTHER INFORMATION: diphenylalanine

<400> SEQUENCE: 32

Lys Trp Trp Lys Lys Xaa Trp Lys Lys
1               5

<210> SEQ ID NO 33
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: biphenylalanine

<400> SEQUENCE: 33

Arg Arg Xaa Trp Arg Arg Trp Trp Arg
1               5

<210> SEQ ID NO 34
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: diphenylalanine

<400> SEQUENCE: 34

Arg Arg Xaa Trp Arg Arg Trp Trp Arg
1               5

<210> SEQ ID NO 35
<211> LENGTH: 9
<212> TYPE: PRT
<213> ORGANISM: Artificial
<220> FEATURE:
<223> OTHER INFORMATION: Synthetic sequence
```

```
<220> FEATURE:
<221> NAME/KEY: MISC_FEATURE
<222> LOCATION: (1)..(9)
<223> OTHER INFORMATION: D-amino acid
<220> FEATURE:
<221> NAME/KEY: MISC_FEATURE
<222> LOCATION: (3)..(3)
<223> OTHER INFORMATION: biphenylalanine

<400> SEQUENCE: 35

Lys Lys Xaa Trp Lys Lys Trp Trp Lys
1               5

<210> SEQ ID NO 36
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (3)..(3)
<223> OTHER INFORMATION: biphenylalanine
<220> FEATURE:
<221> NAME/KEY: MISC_FEATURE
<222> LOCATION: (4)..(9)
<223> OTHER INFORMATION: D-amino acid

<400> SEQUENCE: 36

Lys Lys Xaa Trp Lys Lys Trp Trp Lys
1               5

<210> SEQ ID NO 37
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: D-amino acid

<400> SEQUENCE: 37

Lys Lys Xaa Trp Lys Lys Trp Trp Lys
1               5

<210> SEQ ID NO 38
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(2)
<223> OTHER INFORMATION: Dbu
<220> FEATURE:
<221> NAME/KEY: MISC_FEATURE
<222> LOCATION: (4)..(4)
<223> OTHER INFORMATION: diphenylalanine
<220> FEATURE:
<221> NAME/KEY: MISC_FEATURE
<222> LOCATION: (5)..(6)
<223> OTHER INFORMATION: Dbu
<220> FEATURE:
<221> NAME/KEY: MISC_FEATURE
<222> LOCATION: (9)..(9)
<223> OTHER INFORMATION: Dbu
```

```
<400> SEQUENCE: 38

Xaa Xaa Trp Xaa Xaa Xaa Trp Trp Xaa
1               5

<210> SEQ ID NO 39
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: 1-naphthylalanine

<400> SEQUENCE: 39

Lys Lys Trp Xaa Lys Lys Trp Trp Lys
1               5

<210> SEQ ID NO 40
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: 2-naphthylalanine

<400> SEQUENCE: 40

Lys Lys Trp Xaa Lys Lys Trp Trp Lys
1               5

<210> SEQ ID NO 41
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: 2-amino-3-(anthracen-9-yl)propanoic acid

<400> SEQUENCE: 41

Lys Lys Trp Xaa Lys Lys Trp Trp Lys
1               5

<210> SEQ ID NO 42
<211> LENGTH: 9
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: 2-amino-3-[1,1':4',1"-terphenyl-4-yl]propionic
      acid

<400> SEQUENCE: 42

Lys Lys Trp Xaa Lys Lys Trp Trp Lys
1               5
```

NONAPEPTIDE WITH ANTI-TUMOUR ACTIVITY

The present application is the U.S. National Phase of International patent application Ser. No. PCT/EP2009/006744, filed on Sep. 11, 2009, which claims priority to U.K. Patent Application Serial No. 0821616.0, filed Nov. 26, 2008, both of which are hereby incorporated by reference in their entireties.

The present invention relates to peptides or peptide like molecules and their uses in therapy, in particular as anti-tumour agents and also as adjuvants for vaccines including tumour vaccines.

Peptides and their derivatives have long been recognised as therapeutically interesting molecules. A wide variety of organisms use peptides as part of their host defense mechanism. Antimicrobial peptides have been isolated from species as diverse as bacteria and mammals. Generally, these peptides have a net positive charge and a propensity to form amphiphilic α-helix or β-sheet structures upon interaction with the outer phospholipid bilayer in bacterial cell membranes. In most cases the detailed molecular mechanisms of the antibiotic action are unknown, although some peptides categorized as class L (lytic) peptides are believed to interact with bacterial cell membranes, forming ion-channels, pores or other structures capable of destabilizing the membrane.

Amongst the general class of lytic antimicrobial peptides, some have also been shown to have anti-tumour activity. Eukaryotic cell membranes of tumour cells develop properties similar to the cell membranes of prokaryotes and it has been postulated that this could provide a degree of selectivity of these lytic peptides for tumour cells in vivo. Some anti-tumour activity of peptides having amphiphilic character and a net positive charge has been described in WO 00/12542, WO 01/66147, WO 01/19852 and by Yang et al. in Journal of Peptide Science [2004], 10, pp 37-46 (PMID: 14959890). Generally anti-tumour activity requires larger peptides than can be designed for antibacterial uses. Balancing the need for good target cell cytotoxicity and in vivo selectivity presents particular problems in the generation of useful anti-tumour peptides, in part because there remains a high degree of similarity between the cell membrane of tumour and non-transformed cells. Nevertheless, the prevalence of cancer in human and animal populations and its role in mortality means there is a continuing need for new drugs which are effective against tumours. Elimination of a tumour or a reduction in its size or reducing the number of cancer cells circulating in the blood or lymph systems may be beneficial in a variety of ways; reducing pain or discomfort, preventing metastasis, facilitating operative intervention, prolonging life.

During their investigations into the biological activity of peptides, the present inventors have identified a small group of molecules which exhibit particularly good activity against a range of cancer types and good selectivity for cancerous cells over normal cells.

As is detailed below, one molecule (LTX-315) is particularly preferred and therefore according to a first aspect of the present invention there is provided a compound having the formula of SEQ ID NO: 23, or a salt, ester or amide thereof.

In one aspect, the present invention provides a compound, preferably a peptide, having the following characteristics:
a) consisting of 9 amino acids in a linear arrangement;
b) of those 9 amino acids, 5 are cationic and 4 have a lipophilic R group;
c) at least one of said 9 amino acids is a non-genetically coded amino acid or a modified derivative of a genetically coded amino acid; and optionally
d) the lipophilic and cationic residues are arranged such that there are no more than two of either type of residue adjacent to one another; and further optionally
e) the molecule comprises two pairs of adjacent cationic amino acids and one or two pairs of adjacent lipophilic residues.

The cationic amino acids, which may be the same or different, are preferably lysine or arginine but may be histidine or any non-genetically coded or modified amino acid carrying a positive charge at pH 7.0.

Suitable non-genetically coded cationic amino acids and modified cationic amino acids include analogues of lysine, arginine and histidine such as homolysine, ornithine, diaminobutyric acid, diaminopimelic acid, diaminopropionic acid and homoarginine as well as trimethylysine and trimethylornithine, 4-aminopiperidine-4-carboxylic acid, 4-amino-1-carbamimidoylpiperidine-4-carboxylic acid and 4-guanidinophenylalanine.

The lipophilic amino acids (i.e. amino acids with a lipophilic R group), which may be the same or different, all possess an R group with at least 7, preferably at least 8 or 9, more preferably at least 10 non-hydrogen atoms. An amino acid with a lipophilic R group is referred to herein as a lipophilic amino acid. Typically the lipophilic R group has at least one, preferably two cyclic groups, which may be fused or connected.

The lipophilic R group may contain hetero atoms such as O, N or S but typically there is no more than one heteroatom, preferably it is nitrogen. This R group will preferably have no more than 2 polar groups, more preferably none or one, most preferably none.

Tryptophan is a preferred lipophilic amino acid and the molecules preferably comprise 1 to 3, more preferably 2 or 3, most preferably 3 tryptophan residues. Further genetically coded lipophilic amino acids which may be incorporated are phenylalanine and tyrosine.

Preferably one of the lipophilic amino acids is a non-genetically coded amino acid. Most preferably the molecule consists of 3 genetically coded lipophilic amino acids, 5 genetically coded cationic amino acids and 1 non-genetically coded lipophilic amino acid. In this context, a D amino acid, while not strictly genetically coded, is not considered to be a "non-genetically coded amino acid", which should be structurally, not just stereospecifically, different from the 20 genetically coded L amino acids. The molecules of the invention may have some or all of the amino acids present in the D form, preferably however all amino acids are in the L form.

When the molecules include a non-genetically coded lipophilic amino acid (or amino acid derivative), the R group of that amino acid preferably contains no more than 35 non-hydrogen atoms, more preferably no more than 30, most preferably no more than 25 non-hydrogen atoms.

Preferred non-genetically coded amino acids include: 2-amino-3-(biphenyl-4-yl)propanoic acid (biphenylalanine), 2-amino-3,3-diphenylpropanoic acid (diphenylalanine), 2-amino-3-(anthracen-9-yl)propanoic acid, 2-amino-3-(naphthalen-2-yl)propanoic acid, 2-amino-3-(naphthalen-1-yl)propanoic acid, 2-amino-3-[1,1':4',1''-terphenyl-4-yl]-propionic acid, 2-amino-3-(2,5,7-tri-tert-butyl-1H-indol-3-yl)propanoic acid, 2-amino-3-[1,1':3',1''-terphenyl-4-yl]-propionic acid, 2-amino-3-[1,1':2',1''-terphenyl-4-yl]-propionic acid, 2-amino-3-(4-naphthalen-2-yl-phenyl)-propionic acid, 2-amino-3-(4'-butylbiphenyl-4-yl)propanoic acid, 2-amino-3-[1,1':3',1''-terphenyl-5'-yl]-propionic acid and 2-amino-3-(4-(2,2-diphenylethyl)phenyl)propanoic acid.

In a preferred embodiment the compounds of the invention have one of formulae I to V listed below, in which C represents a cationic amino acid as defined above and L represents a lipophilic amino acid as defined above. The amino acids being covalently linked, preferably by peptide bonds resulting in a true peptide or by other linkages resulting in a peptidomimetic. The free amino or carboxy terminals of these molecules may be modified, the carboxy terminus is preferably modified to remove the negative charge, most preferably the carboxy terminus is amidated, this amide group may be substituted.

```
CCLLCCLLC (I)      (SEQ ID NO: 1)
LCCLLCCLC (II)     (SEQ ID NO: 2)
CLLCCLLCC (III)    (SEQ ID NO: 3)
CCLLCLLCC (IV)     (SEQ ID NO: 4)
CLCCLLCCL (V)      (SEQ ID NO: 5)
```

A peptidomimetic is typically characterised by retaining the polarity, three dimensional size and functionality (bioactivity) of its peptide equivalent but wherein the peptide bonds have been replaced, often by more stable linkages. By 'stable' is meant more resistant to enzymatic degradation by hydrolytic enzymes. Generally, the bond which replaces the amide bond (amide bond surrogate) conserves many of the properties of the amide bond, e.g. conformation, steric bulk, electrostatic character, possibility for hydrogen bonding etc. Chapter 14 of "Drug Design and Development", Krogsgaard, Larsen, Liljefors and Madsen (Eds) 1996, Horwood Acad. Pub provides a general discussion of techniques for the design and synthesis of peptidomimetics. In the present case, where the molecule is reacting with a membrane rather than the specific active site of an enzyme, some of the problems described of exactly mimicking affinity and efficacy or substrate function are not relevant and a peptidomimetic can be readily prepared based on a given peptide structure or a motif of required functional groups. Suitable amide bond surrogates include the following groups: N-alkylation (Schmidt, R. et al., Int. J. Peptide Protein Res., 1995, 46, 47), retro-inverse amide (Chorev, M and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391).

The peptidomimetic compounds of the present invention may have 9 identifiable sub-units which are approximately equivalent in size and function to the 9 cationic and lipophilic amino acids. The term 'amino acid' may thus conveniently be used herein to refer to the equivalent sub-units of a peptidomimetic compound. Moreover, peptidomimetics may have groups equivalent to the R groups of amino acids and discussion herein of suitable R groups and of N and C terminal modifying groups applies, mutatis mutandis, to peptidomimetic compounds.

As is discussed in "Drug Design and Development", Krogsgaard et al., 1996, as well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Peptidomimetics and thus peptidomimetic backbones wherein just the amide bonds have been replaced as discussed above are, however, preferred.

Suitable peptidomimetics include reduced peptides where the amide bond has been reduced to a methylene amine by treatment with a reducing agent e.g. borane or a hydride reagent such as lithium aluminium-hydride. Such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142. Strongly basic conditions will favour N-methylation over O-methylation and result in methylation of some or all of the nitrogen atoms in the peptide bonds and the N-terminal nitrogen.

Preferred peptidomimetic backbones include polyesters, polyamines and derivatives thereof as well as substituted alkanes and alkenes. The peptidomimetics will preferably have N and C termini which may be modified as discussed herein.

β and γ amino acids as well as α amino acids are included within the term 'amino acids', as are N-substituted glycines. The compounds of the invention include beta peptides and depsipeptides.

As discussed above, the compounds of the invention incorporate at least one, and preferably one, non-genetically coded amino acid. When this residue is denoted L', preferred compounds are represented by the following formulae:

```
CCL'LCCLLC (I')      (SEQ ID NO: 6)
CCLLCCLL'C (I'')     (SEQ ID NO: 7)
CCLL'CCLLC (I''')    (SEQ ID NO: 8)
LCCLL'CCLC (II')     (SEQ ID NO: 9)
```

Particularly preferred are peptides of formula I and II, and of these, peptides of formula I" are especially preferred.

Preferably, the peptide is not LTX-302 (SEQ ID NO: 11) (below).

The following peptides as presented in Table 1 (with the exception of LTX-302) are most preferred.

TABLE 1

| Name | SEQ ID NO | Sequence |
| --- | --- | --- |
| LTX-301 | 10 | Dip-K-K-W-W-K-K-W-K-NH$_2$ |
| LTX-302 | 11 | W-K-K-W-Dip-K-K-W-K-NH$_2$ |
| LTX-303 | 12 | W-K-K-W-W-K-K-Dip-K-NH$_2$ |
| LTX-304 | 13 | *Bip*-K-K-W-W-K-K-W-K-NH$_s$ |
| LTX-305 | 14 | W-K-K-*Bip*-W-K-K-W-K-NH$_2$ |
| LTX-306 | 15 | w-k-k-w-dip-k-k-w-k-NH$_2$ |
| LTX-307 | 16 | K-K-W-Dip-K-K-W-W-K-NH$_2$ |
| LTX-308 | 17 | k-k-W-Dip-k-k-W-W-k-NH$_2$ |

TABLE 1-continued

| Name | SEQ ID NO | Sequence |
|---|---|---|
| LTX-309 | 18 | K-K-W-Dip-K-K-W-Dip-K-NH$_2$ |
| LTX-310 | 19 | K-K-W-*Bip*-K-K-W-W-K-NH$_2$ |
| LTX-312 | 20 | K-*Bip*-K-K-W-W-K-K-W-NH$_2$ |
| LTX-313 | 21 | K-K-*Bip*-W-K-K-W-W-K-NH$_2$ |
| LTX-314 | 22 | K-K-W-W-K-K-Dip-W-K-NH$_2$ |
| LTX-315 | 23 | K-K-W-W-K-K-W-Dip-K-NH$_2$ |
| LTX-316 | 24 | K-W-Dip-K-K-W-W-K-K-NH$_2$ |
| LTX-317 | 25 | K-K-W-W-K-W-Dip-K-K-NH$_2$ |
| LTX-318 | 26 | Orn-Orn-W-Dip-Orn-Orn-W-W-Orn-NH$_2$ |
| LTX-319 | 27 | Dap-Dap-W-Dip-Dap-Dap-W-W-Dap-NH$_2$ |
| LTX-320 | 28 | R-R-W-Dip-R-R-W-W-R-NH$_2$ |
| LTX-321 | 29 | K-W-W-K-Dip-W-K-K-NH$_2$ |
| LTX-323 | 30 | K-Dip-K-K-W-W-K-K-W-NH$_2$ |
| LTX-324 | 31 | K-K-Dip-W-K-K-W-W-K-NH$_2$ |
| LTX-325 | 32 | k-w-w-k-k-dip-w-k-k-NH$_2$ |
| LTX-326 | 33 | R-R-*Bip*-W-R-R-W-W-R-NH$_2$ |
| LTX-327 | 34 | R-R-Dip-W-R-R-W-W-R-NH$_2$ |
| LTX-329 | 35 | k-k-bip-w-k-k-w-w-k-NH$_2$ |
| LTX-331 | 36 | k-k-Bip-w-k-k-w-w-k-NH$_2$ |
| LTX-332 | 37 | K-K-bip-W-K-K-W-W-K-NH$_2$ |
| LTX-333 | 38 | Dab-Dab-W-Dip-Dab-Dab-W-W-Dab-NH$_2$ |
| LTX-334 | 39 | K-K-W-1-Nal-K-K-W-W-K-NH$_2$ |
| LTX-335 | 40 | K-K-W-2-Nal-K-K-W-W-K-NH$_2$ |
| LTX-336 | 41 | K-K-W-Ath-K-K-W-W-K-NH$_2$ |
| LTX-338 | 42 | K-K-W-Phe(4-4'Bip)-K-K-W-W-K-NH$_2$ |

In which:
the standard single letter code is used for the genetically coded amino acids
lower case denotes D amino acids
Dip is diphenylalanine
Bip is biphenylalanine
Orn is ornithine
Dap is 2,3-diaminopropionic acid
Dab is 2,4-diaminobutyric acid
1-Nal is 1-naphthylalanine
2-Nal is 2-naphthylalanine
Ath is 2-amino-3-(anthracen-9-yl)propanoic acid
Phe(4,4'Bip) is 2-amino-3-[1,1':4',1''-terphenyl-4-yl]propionic acid All of the molecules described herein may be in salt, ester or amide form.

Thus, also provided according to the present invention is a compound selected from the group consisting of: LTX-301, LTX-303-LTX-310, LTX-312-LTX-321, LTX-323-LTX-327, LTX-329, LTX-331-LTX-336, and LTX-338, or a salt, ester or amide thereof. Thus, the present invention provides a compound having a formula selected from the group consisting of: SEQ ID NOs: 10 and 12-42, or a salt, ester or amide thereof.

The molecules are preferably peptides and preferably have a modified, particularly an amidated, C-terminus. Amidated peptides may themselves be in salt form and acetate forms are preferred. Suitable physiologically acceptable salts are well known in the art and include salts of inorganic or organic acids, and include trifluoroacetate as well as acetate and salts formed with HCl.

The molecules described herein are amphipathic in nature, their 2° structure, which may or may not tend towards the formation of an α-helix, provides an amphipathic molecule in physiological conditions.

In a further aspect is provided the compounds of the invention, in particular the compounds of formulae I to V, especially the peptides of Table 1, for use in therapy, particularly for use as an anti-tumour or anticancer agent, the terms are used synonymously herein.

The compounds exhibit anti-tumour activity; in particular they exert a cytotoxic effect through a direct membrane-affecting mechanism. These molecules are lytic, destabilizing or even perforating the cell membrane. This offers a distinct therapeutic advantage over agents which act on or interact with proteinaceous components of the target cells, e.g. cell surface receptors. While mutations may result in new forms of the target proteins leading to chemotherapeutic resistance, it is much less likely that radical changes to the lipid membranes could occur to prevent the cytotoxic effect.

Thus in a further aspect is provided the compounds of the invention for use in destabilizing and/or permeabilising tumour cell membranes. By 'destabilizing' is meant a perturbation of the normal three dimensional lipid bi-layer configuration including but not limited to membrane thinning, increased membrane permeability (typically not involving channels) to water, ions or metabolites etc.

The invention provides methods of treating tumours, both solid and nonsolid tumours, by administering the various compounds described herein. The amount administered should be effective to kill all or a proportion of the target cells or to prevent or reduce their rate of multiplication, or to inhibit metastasis or otherwise to lessen the harmful effect of the tumour on the patient. The clinician or patient should observe improvement in one or more of the parameters or symptoms associated with the tumour. Administration may also be prophylactic. The patient will typically be a human patient but non-human animals, such as domestic or livestock animals may also be treated.

Unlike the majority of agents which have protein targets, the molecules of the present invention can target a wide variety of cancers, as shown in the Examples hereto. Preferred cancer targets include lymphomas, leukemias, neuroblastomas and glioblastomas (e.g. from the brain), carcinomas and adenocarcinomas (particularly from the breast, colon, kidney, liver, lung, ovary, pancreas, prostate and skin) and melanomas. Breast cancer is an especially preferred target.

The peptides of the invention may be synthesised in any convenient way. Generally the reactive groups present (for example amino, thiol and/or carboxyl) will be protected during overall synthesis. The final step in the synthesis will thus be the deprotection of a protected derivative of the invention.

In building up the peptide, one can in principle start either at the C-terminal or the N-terminal although the C-terminal starting procedure is preferred.

Methods of peptide synthesis are well known in the art but for the present invention it may be particularly convenient to carry out the synthesis on a solid phase support, such supports being well known in the art.

A wide choice of protecting groups for amino acids are known and suitable amine protecting groups may include carbobenzyloxy (also designated Z) t-butoxycarbonyl (also designated Boc), 4-methoxy-2,3,6-trimethylbenzene sulphonyl (Mtr) and 9-fluorenylmethoxy-carbonyl (also designated Fmoc). It will be appreciated that when the peptide is built up from the C-terminal end, an amine-protecting group will be present on the α-amino group of each new residue added and will need to be removed selectively prior to the next coupling step.

Carboxyl protecting groups which may, for example be employed include readily cleaved ester groups such as benzyl (Bzl), p-nitrobenzyl (ONb), or t-butyl (OtBu) groups as well as the coupling groups on solid supports, for example the Rink amide linked to polystyrene.

Thiol protecting groups include p-methoxybenzyl (Mob), trityl (Trt) and acetamidomethyl (Acm).

Preferred peptides of the invention may conveniently be prepared using the t-butyloxycarbonyl (Boc) protecting group for the amine side chains of Lys, Orn, Dab and Dap as well as for protection of the indole nitrogen of the tryptophan residues. Fmoc can be used for protection of the alpha-amino groups. For peptides containing Arg, 2,2,4,6,7-pentamethyldihydrobenzofurane-5-sulfonyl can be used for protection of the guanidine side chain.

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoroacetic acid. Thiol protecting groups such as Trt may be removed selectively using an oxidation agent such as iodine.

References and techniques for synthesising peptidomimetic compounds and the other bioactive molecules of the invention are described herein and thus are well known in the art.

Formulations comprising one or more compounds of the invention in admixture with a suitable diluent, carrier or excipient constitute a further aspect of the present invention. Such formulations may be for, inter alia, pharmaceutical (including veterinary) purposes. Suitable diluents, excipients and carriers are known to the skilled person.

While it is possible for the compounds of the present invention (or salts, esters or amides thereof) to be administered as pure compounds, it is preferable to present them as pharmaceutical formulations. Thus, formulations according to the present invention preferably comprise at least one compound, salt, ester or amide as defined above, together with at least one other therapeutic ingredient. Thus, the present invention extends to combination products incorporating the compound of the present invention (or a salt, ester or amide thereof) and at least one other therapeutic ingredient.

Methods of treating tumours which comprise administration to a human or animal patient one or more of the compounds as defined herein constitute a further aspect of the present invention.

The compositions according to the invention may be presented, for example, in a form suitable for oral, topical, nasal, parenteral, intravenal, intratumoral, rectal or regional (e.g. isolated limb perfusion) administration. Administration is typically by a parenteral route, preferably by injection subcutaneously, intramuscularly, intracapsularly, intraspinaly, intratumouraly or intravenously.

The active compounds defined herein may be presented in the conventional pharmacological forms of administration, such as tablets, coated tablets, nasal sprays, solutions, emulsions, liposomes, powders, capsules or sustained release forms. Conventional pharmaceutical excipients as well as the usual methods of production may be employed for the preparation of these forms.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Preferred formulations are those in which the peptides are dissolved in saline. Such formulations being suitable for use in preferred methods of administration, especially local administration, i.e. intratumoral, e.g. by injection or by perfusion/infusion of a preferably isolated (including partial isolation) limb, body region or organ.

Dosage units containing the active molecules preferably contain 0.1-10 mg, for example 1-5 mg of the anti-tumour agent. The pharmaceutical compositions may additionally comprise further active ingredients, including other cytotoxic agents such as other anti-tumour peptides. Other active ingredients may include different types of cytokines e.g. IFN-γ, TNF, CSF and growth factors, immunomodulators, chemotherapeutics e.g. cisplatin or antibodies or cancer vaccines.

In employing such compositions systemically, the active molecule is present in an amount to achieve a serum level of the bioactive molecule of at least about 5 μg/ml. In general, the serum level need not exceed 500 μg/ml. A preferred serum level is about 100 μg/ml. Such serum levels may be achieved by incorporating the bioactive molecule in a composition to be administered systemically at a dose of from 1 to about 10 mg/kg. In general, the molecule(s) need not be administered at a dose exceeding 100 mg/kg.

Also provided according to the present invention is a compound, salt, ester or amide according to the present invention in combination with an at least one vaccine.

As detailed below, experiments have shown that prophylactic vaccination with LTX-315-lysed tumour cells result in tumour growth inhibition and show that the compounds of the present invention are highly effective as vaccine adjuvants, and thus the present invention extends to the use of the compounds (or salts, esters or amides thereof) in combination with an at least one vaccine. Preferred vaccines include, but are not limited to, anti cancer vaccines containing at least one protein and/or peptide with amino acid sequences corresponding to immunogenic sequence(s) from tumour associated antigen(s) (TAA), preferred TAAs, but not limited to, are telomerase, survivin oncogenic p21 ras, abl, gip, gsp, ret, terk, and antivirus vaccines containing at least one protein and/or peptide with amino acid sequence(s) corresponding to immunogenic sequences from viral protein(s). In addition, tumour lysate can be used. Examples of preferred vaccines include vaccines, peptides, peptide fragments and immunogens taught by WO 92/14756, WO 00/66153 (NO 309798), WO 00/02581, WO 02/051994, WO 02/070679, WO 02/094312, WO 99/58552, and WO 99/58564.

Also provided according to the present invention is the use of a compound, salt, ester or amide or combination according to the present invention in the manufacture of a medicament, particularly in the manufacture of a medicament for the treatment of cancer and/or in the manufacture of a vaccine.

Preferably, the medicament is for the treatment of multidrug resistant (MDR) tumours.

Also provided according to the present invention is a pharmaceutical pack comprising:
(i) an at least one vaccine; and
(ii) a compound, salt, ester or amide according to the present invention.

With pharmaceutical packs, the at least one vaccine and the compound, salt, ester or amide can for administration separately (for example with a time delay of about, at least, or no more than 1, 2, 3, 4, 5, 10, 15, 20, 25, 30, 45, 60, 90 or 120 minutes). The pharmaceutical pack can of course also comprise instructions for administration.

Also provided according to the present invention is a method of treatment of a tumour, comprising the step of administering a pharmaceutically effective amount of a compound, salt, ester or amide or combination according to the present invention to a patient in need of same.

Also provided according to the present invention is a method of vaccination, comprising the step of administering a pharmaceutically effective amount of a compound, salt, ester or amide or combination according to the present invention to a patient.

Also provided according to the present invention is a method of manufacture of a medicament, comprising admixing a compound having the formula of SEQ ID NO: 23 (LTX-315) or a salt, ester or amide thereof with a pharmaceutically acceptable carrier, diluent or excipient.

Also provided according to the present invention is a method of manufacture of a medicament, comprising admixing a compound having the formula of SEQ ID NO: 23 (LTX-315) or a salt, ester or amide thereof with tumour cells.

Figure 2:
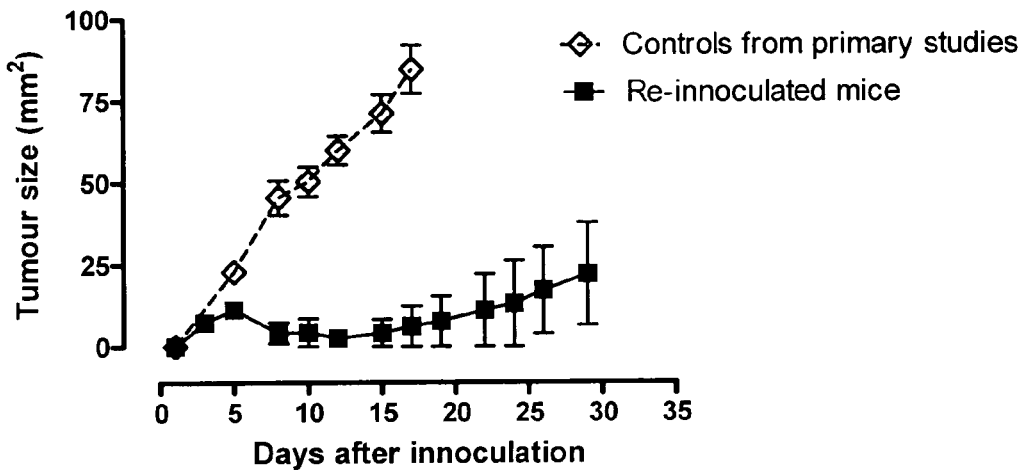
Figure 3:
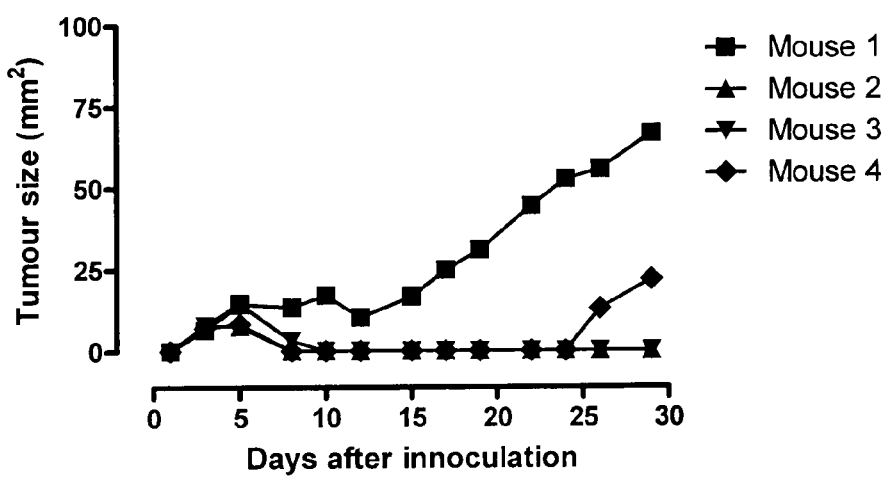
Figure 6:
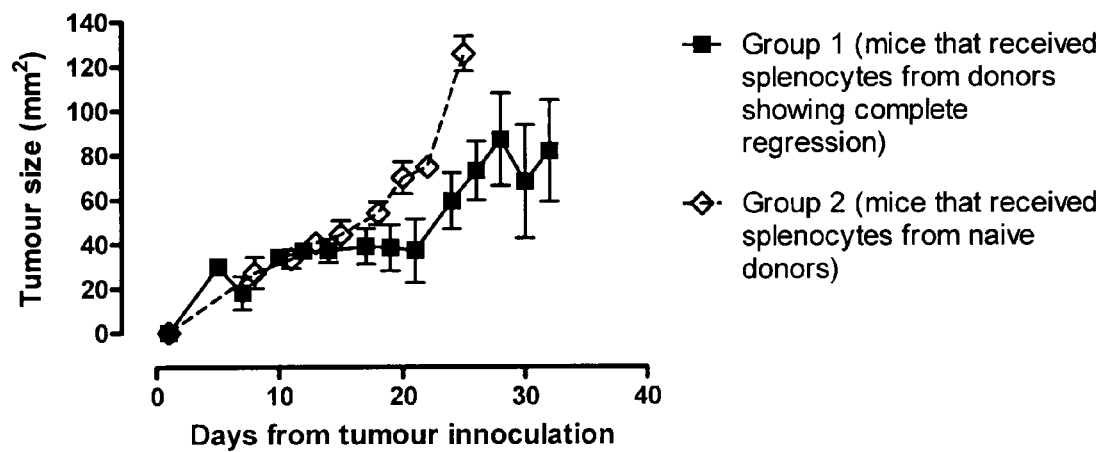
Figure 7:
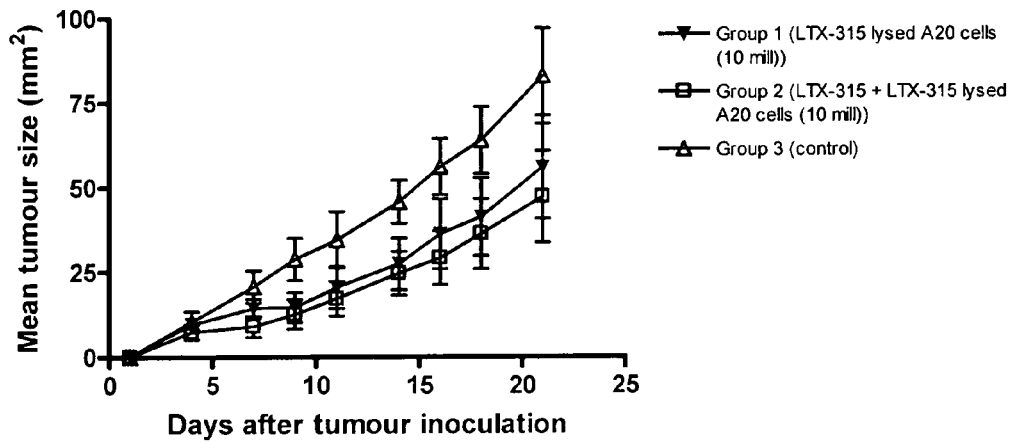

The invention will now be further described in the following Examples and with reference to the figures in which:

FIG. 1 is a graph showing the percentage of red blood cell death in a series of experiments to test peptide LTX-315 at varying concentrations. X-axis shows peptide concentration (μg/ml). Y-axis shows % cell death;

FIG. 2 shows tumour growth in mice re-inoculated with murine A20 B cell lymphoma cells compared with growth in the control animals from the initial study. Diamonds indicate controls from primary studies. Solid squares indicate re-inoculated mice;

FIG. 3 shows tumour growth in individual mice re-inoculated with murine A20 B cell lymphoma cells having been initially treated with LTX-315. Squares indicate Mouse 1. Triangles (base at bottom) indicate Mouse 2. Triangles (base at top) indicate Mouse 3. Diamonds indicate Mouse 4;

Figures 4, 5:
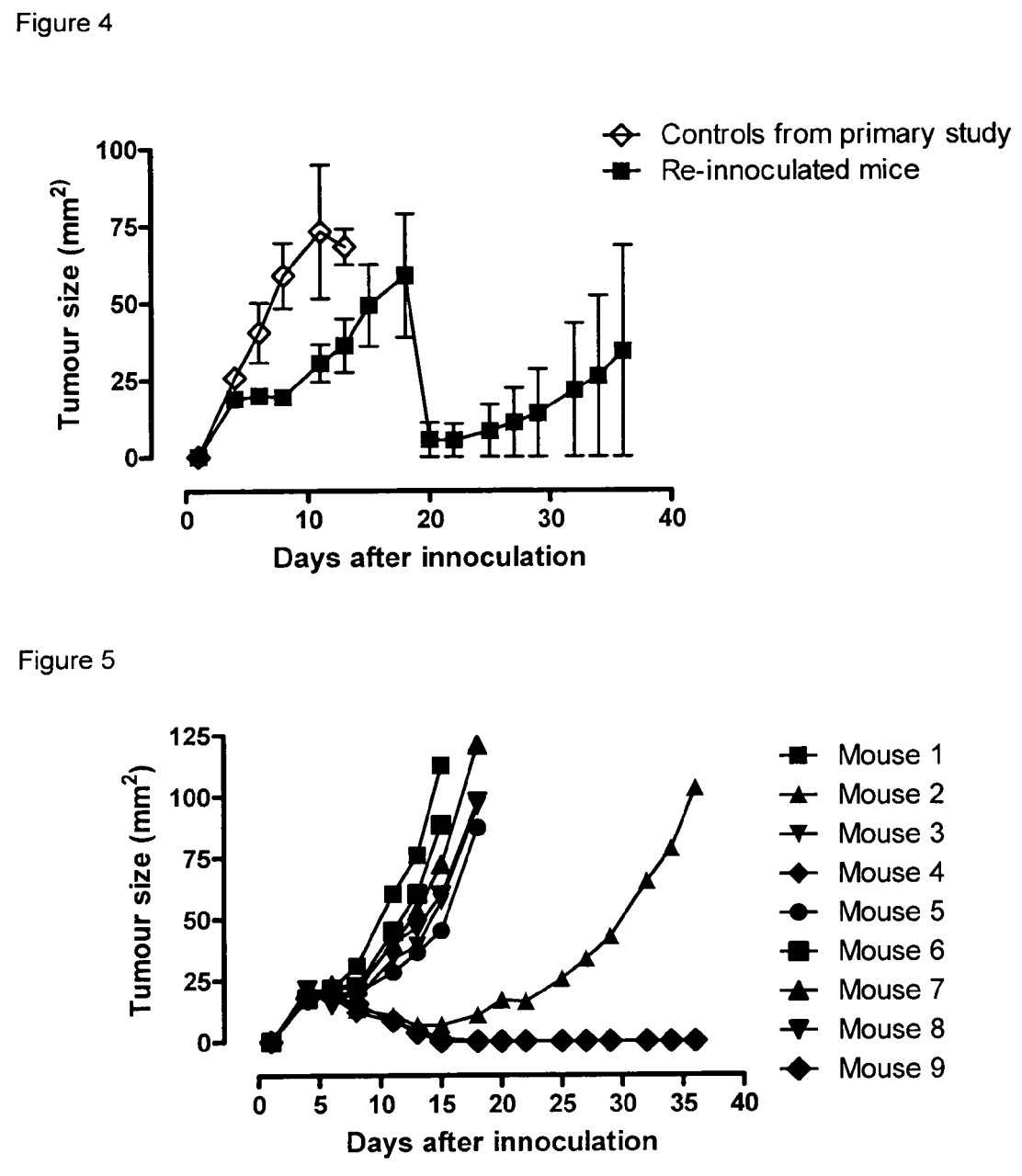

FIG. 4 shows tumour growth in mice re-inoculated with murine CT26WT colon carcinoma cells compared with growth in the control animals. Diamonds indicate controls from primary studies. Solid squares indicate re-inoculated mice;

FIG. 5 shows tumour growth in individual mice re-inoculated with murine CT26WT colon carcinoma cells having been initially treated with LTX-315. Small squares indicate Mouse 1. Small triangles (base at bottom) indicate Mouse 2. Small triangles (base at top) indicate Mouse 3. Small diamonds indicate Mouse 4; Circles indicate Mouse 5. Large squares indicate Mouse 6. Large triangles (base at bottom) indicate Mouse 7. Large triangles (base at top) indicate Mouse 8. Large diamonds indicate Mouse 9;

FIG. 6 shows growth of A20 B-cell lymphomas in irradiated mice that received splenocytes from donor mice showing complete tumour regression following treatment with LTX-315 (Group 1) or control mice (Group 2) that received splenocytes from naïve donor mice. Squares indicate Group 1 (mice that received splenocytes from donors showing complete regression). Diamonds indicate Group 2 (mice that received splenocytes from naive donors);

FIG. 7 shows anti-cancer effect of two different treatment regimes on solid murine A20 tumours (Groups 1 and 2) as compared to non-treated controls (Group 3). Inverted solid triangles (base at top) indicate Group 1 (treatment). Open squares indicate Group 2 (treatment+adjuvant). Open triangles (base at bottom) indicate Group 3 (control). Order of tumour size (mm$^2$) at Day 21 is (largest to smallest): Group 3, Group 1, Group 2.

In summary, the Examples below show:
Example 1—that LTX-315 is the most potent of the 5 tested compounds in an in vitro cytotoxic activity study against a panel of 37 human cancer cell lines.
Example 2—that LTX-315 is the most potent of the 5 tested compounds in an in vitro cytotoxic activity study against a panel of 10 lymphoma cell lines.
Example 3—that LTX 315 has a mean $EC_{50}$ value greater than 1200 μg/ml (833 μM) against human red blood cells.
Example 4—that the anti-tumour activity of LTX-315 resulted in a complete tumour response in 3 of 7 treated mice for the Group receiving the optimal dose (Group 1) in an investigation into the effect of LTX-315 at different dose levels on a murine A20 B-cell lymphoma in mice.
Example 5—that four different LTX-315 treatment regimes demonstrated a strong anti tumour effect against murine CT26WT (multidrug resistant) tumours.
Example 6—that LTX-315 has a broad spectrum of activity against various multidrug resistant cancer cell lines and, significantly, a much weaker cytotoxic effect on normal human cells.
Example 7—that complete tumour regression following initial treatment of solid murine tumours with LTX-315 resulted in a form of endogenous long-term protection against growth of the same tumours following re-inoculation.
Example 8—that treatment with LTX-315 may confer long term protection against specific tumours by eliciting an immune response.
Example 9—that an anti A20 cell immune response have been induced by the injection of the cocktail of LTX-315 and lysed A20 cells.

EXAMPLE 1

In vitro Cytotoxic Activity Study of 5 Test Compounds Against a Panel of 37 Human Cancer Cell Lines 1. Study Aim
   To determine the concentrations of five novel compounds to obtain a 50% inhibition of proliferation ($IC_{50}$) against a panel of 37 human cancer cell lines.
2. Materials and Methods
2.1. Test Substances
2.1.1. Test Substances
   Test substances, LTX-302, LTX-313, LTX-315, LTX-320 and LTX-329 (see Table 1) provided in powder form.
2.1.2. Positive Control
   Triton X-100 was used as positive control, supplied by Oncodesign (Dijon, France) from Sigma (Saint Quentin Fallavier, France).
2.1.3. Drug Vehicle and Storage Conditions
   Compounds were stored at 4° C. Powder was first dissolved in serum free culture medium (RPMI 1640, Lonza, Verviers, Belgium) and further diluted using serum-free culture medium to reach appropriate dilutions. Stock solution was not stored and was prepared fresh the day of experiment.

1% (final concentration) Triton X-100 was obtained by dilution using culture medium.

2.2. Tumor Cell Lines and Culture Conditions 2.2.1. Tumor Cell Lines

Cancer cell lines and culture media were purchased and provided by Oncodesign.

| Cell lines | Origin | Source |
|---|---|---|
| BLOOD | | |
| CCRF-CEM | acute lymphoblastic leukemia, T cells | Pharmacell[a] |
| CCRF-CEM/VLB | acute lymphoblastic leukemia, T cells | Pharmacell |
| HL-60 | acute promyelocytic leukemia, AML, pluripotent differentiation | ATCC[b] |
| HL-60/ADR | acute promyelocytic leukemia, AML | Pharmacell |
| K-562 | chronic myeloid leukemia, pleural effusion metastasis | ATCC |
| K-562/Gleevec | chronic myeloid leukemia, pleural effusion metastasis | Oncodesign |
| RPMI 8226 | myeloma, B cells, Igl-type | Pharmacell |
| BRAIN | | |
| SH-SY5Y | neuroblastoma, bone marrow metastasis | ATCC |
| SK-N-AS | neuroblastoma, bone marrow metastasis | ATCC |
| U-87 MG | glioblastoma, astrocytoma | ATCC |
| BREAST | | |
| MCF-7 | invasive ductal carcinoma, pleural effusion metastasis | Pharmacell |
| MCF7/mdr | adenocarcinoma, pleural effusion metastasis | Pharmacell |
| MDA-MB-231 | invasive ductal carcinoma, pleural effusion metastasis | Pharmacell |
| MDA-MB-435S | invasive ductal carcinoma, pleural effusion metastasis | ATCC |
| T-47D | invasive ductal carcinoma, pleural effusion metastasis | ATCC |
| COLON | | |
| COLO 205 | colorectal adenocarcinoma, ascites metastasis | ATCC |
| HCT 116 | colorectal carcinoma | ATCC |
| HCT-15 | colorectal adenocarcinoma | ATCC |
| HT-29 | colorectal adenocarcinoma | ATCC |
| ENDOTHELIUM | | |
| HUV-EC-C | normal | ATCC |
| KIDNEY | | |
| 786-O | renal cell adenocarcinoma | ATCC |
| A-498 | carcinoma | ATCC |
| LIVER | | |
| Hep G2 | hepatocellular carcinoma | ATCC |
| SK-HEP-1 | adenocarcinoma, ascites metastasis | ATCC |
| LUNG | | |
| A549 | carcinoma | Pharmacell |
| Calu-6 | anaplastic carcinoma | ATCC |
| NCI-H460 | carcinoma, pleural effusion metastasis | ATCC |
| OVARY | | |
| IGROV-1 | carcinoma | Pharmacell |
| IGROV-1/CDDP | carcinoma | Pharmacell |
| NIH:OVCAR-3 | adenocarcinoma, ascites metastasis | Pharmacell |
| SK-OV-3 | adenocarcinoma, ascites metastasis | Pharmacell |
| PANCREAS | | |
| BxPC-3 | adenocarcinoma | ATCC |
| PANC-1 | carcinoma | ATCC |
| PROSTATE | | |
| DU 145 | carcinoma, brain metastasis | Pharmacell |
| PC-3 | adenocarcinoma, bone metastasis | ATCC |
| SKIN | | |
| A-431 | epidermoid carcinoma | ATCC |
| Malme-3M | Malignant melanoma | ATCC |
| SK-MEL-2 | malignant melanoma, skin metastasis | ATCC |

[a]Pharmacell, Paris
[b]ATCC, Manassas, Virginia, USA 2.2.2. Culture Conditions

Tumor cells were grown as adherent monolayers or as suspensions at 37° C. in a humidified atmosphere (5% $CO_2$, 95% air). The culture medium was RPMI 1640 containing 2 mM L-glutamine (Lonza, Belgium) and supplemented with 10% fetal bovine serum (FBS, Lonza). For experimental use, the adherent cells were detached from the culture flask by a 5-minute treatment with trypsin-versene (Lonza), diluted in Hanks' medium without calcium or magnesium (Lonza) and neutralized by addition of complete culture medium. Cells were counted in a hemocytometer and their viability was assessed by 0.25% trypan blue exclusion.

Mycoplasma detection was performed using the MycoAlert® Mycoplasma Detection Kit (Lonza) in accordance with the manufacturer's instructions. All tested cells were found to be negative for mycoplasma contamination.

3. Experimental Design and Treatments 3.1. Cell Lines Amplification and Plating

Tumor cells were plated in 96-well flat-bottom microtitration plates (Nunc, Dutscher, Brumath, France) and incubated at 37° C. for 24 hours before treatment in 190 μl of drug-free culture medium supplemented or not with 10% FBS for adherent or suspension growing cell lines, respectively.

Implantation densities for each cell lines are summarized in Table 2 below:

TABLE 2

| Cell lines | Implantation densities (cells/well) |
|---|---|
| CCRF-CEM | 25,000 |
| CCRF-CEM/VLB | 25,000 |
| HL-60 | 20,000 |
| HL-60/ADR | 20,000 |
| K-562 | 20,000 |
| K-562/IMR | 20,000 |
| RPMI 8226 | 20,000 |
| SH-SY5Y | 20,000 |
| SK-N-AS | 15,000 |
| U-87 MG | 15,000 |
| MCF-7 | 20,000 |
| MCF7/mdr | 20,000 |
| MDA-MB-231 | 15,000 |
| MDA-MB-435S | 20,000 |
| T-47D | 15,000 |
| COLO 205 | 15,000 |
| HCT 116 | 15,000 |
| HCT-15 | 15,000 |
| HT-29 | 20,000 |
| HUV-EC-C | 20,000 |
| 786-O | 15,000 |
| A-498 | 15,000 |

TABLE 2-continued

| Cell lines | Implantation densities (cells/well) |
|---|---|
| Hep G2 | 15,000 |
| SK-HEP-1 | 15,000 |
| A549 | 15,000 |
| Calu-6 | 15,000 |
| NCI-H460 | 15,000 |
| IGROV-1 | 15,000 |
| IGROV-1/CDDP | 15,000 |
| NIH:OVCAR-3 | 15,000 |
| SK-OV-3 | 15,000 |
| BxPC-3 | 15,000 |
| PANC-1 | 15,000 |
| DU 145 | 15,000 |
| PC-3 | 15,000 |
| A-431 | 15,000 |
| Malme-3M | 15,000 |
| SK-MEL-2 | 15,000 |

3.2. $IC_{50}$ Determination

The adherent cell lines were washed once with 200 µl FBS-free culture medium before treatment. Tumor cells were incubated for 4 hours with 10 concentrations of compounds in ¼ dilution step with a top dose of 400 µM (range $4 \times 10^{-4}$ to $4 \times 10^{-10}$ M), with 1% (final concentration) Triton X-100 as positive control and FBS-free culture medium as negative control. The cells (190 µl) were incubated in a 200 µl final volume of FBS-free culture medium containing test substances at 37° C. under 5% $CO_2$.

Three (3) independent experiments were performed, each concentration being tested in quadruplicate. Control cells were treated with vehicle alone. At the end of treatments, the cytotoxic activity was evaluated by a MTS assay (see §3.3).

Dilutions of tested compound as well as distribution to plates containing cells were performed using a Sciclone ALH 3000 liquid handling system (Caliper Life Sciences S.A.). According to automate use, a single range of concentrations was tested whatever the cell lines to be tested. The range was not adapted for each cell line.

3.3. MTS Assay

The in vitro cytotoxic activity of the test substance was revealed by a MTS assay (BALTROP J. A. et al., Bioorg. Med. Chem. Lett. 1991, 1:611-614) using a novel tetrazolium compound (MTS, 3-(4,5-dimethylthiazol-2-yl)-5-(3-carboxymethoxy phenyl)-2-(4-sulfophenyl)-2H-tetrazolium) and an electron coupling reagent named PMS (phenazine methosulfate). Like MTT, MTS is bioreduced by cells into a formazan product that is directly soluble in culture medium without processing, unlike MTT.

At the end of the cells treatment, 40 µl of a 0.22 µm filtered freshly combined solution of MTS (20 ml at 2 mg/ml, Ref G1111, Batch 235897, Exp March/2009, Promega, Charbonnières, France) and PMS (1 ml at 0.92 mg/ml, Ref P9625, Batch 065K0961, Sigma) in Dulbecco's Phosphate Buffered Saline (DPBS, Ref 17-513Q, Batch 6MB0152, Cambrex), were added in each well. Culture plates were incubated for 2 h at 37° C. Absorbency (OD) were measured at 490 nm in each well using VICTOR³™ 1420 multilabeled counter (Wallac, PerkinElmer, Courtaboeuf, France).

4. Data Presentation 4.1. $IC_{50}$ Determination

The dose response inhibition of proliferation (IC) was expressed as follows:

$$IC = \frac{OD_{drug\text{-}exposed\ wells}}{OD_{drug\text{-}free\ walls}} \times 100$$

The OD values are the mean of 4 experimental measurements.

$IC_{50}$: drug concentration to obtain a 50% inhibition of cell proliferation.

The dose-response curves were plotted using XLFit 3 (IDBS, United Kingdom). The $IC_{50}$ determination values were calculated using the XLFit 3 software from semi-log curves. Individual $IC_{50}$ determination values as well as mean and SD values were generated.

4.2. Resistance Index (RI)

Resistance index was calculated using the following formula:

$$RI_{compound\ A} = \frac{IC_{50compound\ A}(\text{Resistant cell line})}{IC_{50compound\ A}(\text{Sensitive cell line})}$$

Resistance index was calculated for each compound for each couple of sensitive and resistant cell lines. Individual resistance index was calculated when $IC_{50}$ values of both sensitive and corresponding resistant cell lines were determined within same experiment. In addition, resistance index was also calculated ratio of mean $IC_{50}$ values obtained during three independent experiments.

5. Results 5.1. LTX-302

All thirty seven (37) human tumor cell lines tested were sensitive to LTX-302 compound with $IC_{50}$ values ranging from 4.83±0.96 µM to 20.09±4.07 µM for T-47D and Hep G2 cell lines, respectively.

Mean $IC_{50}$ value for LTX-302 compound obtained on the 37 tumor cell lines was 12.05±4.27 µM with a median value of 11.70 µM. Mean $IC_{50}$ value obtained for the normal cell line (HUV-EC-C) was higher than for any of the tumor cell lines.

Hematological and lung cancer cell lines were the most sensitive to LTX-302 compound (median $IC_{50}$ values 7.96 µM (n=7) and 9.02 µM (n=3) for hematological and lung cancer cell lines, respectively) whereas liver cancer cell lines were the most resistant (median $IC_{50}$ value 17.84 µM, n=2).

Activity of LTX-302 compound seemed to be slightly decreased by acquired resistance towards doxorubicin as exhibited by the RI values of both HL-60/ADR and MCF-7/mdr cell lines (1.31 and 1.23 for HL-60/ADR and MCF-7/mdr cell lines, respectively). On the contrary, activity of LTX-302 compound seemed to be increased by acquired resistance towards cisplatin as exhibited by a RI value of 0.33 for IGROV-1/CDDP cell line.

5.2. LTX-313

All thirty seven (37) human tumor cell lines tested were sensitive to LTX-313 compound with $IC_{50}$ values ranging from 4.01±0.39 µM to 18.49±4.86 µM for RPMI 8226 and U-87 MG cell lines, respectively.

Mean $IC_{50}$ value for LTX-313 compound obtained on the 37 tumor cell lines was 9.60±3.73 µM with a median value of 8.83 µM. Mean $IC_{50}$ value obtained for the normal cell line (HUV-EC-C) was higher than for any of the tumor cell lines.

Hematological cancer cell lines were the most sensitive to LTX-313 compound (median $IC_{50}$ value 7.04 µM, n=7) whereas liver cancer cell lines were the most resistant (median $IC_{50}$ value 13.71 µM, n=2).

Activity of LTX-313 compound seemed not to be modified by acquired resistance towards doxorubicin as exhibited by the RI values of CCRF-CEM/VLB, HL-60/ADR and MCF-7/mdr cell lines (0.76, 1.16 and 1.24 for CCRF-CEM/VLB, HL-60/ADR and MCF-7/mdr cell lines, respectively). On the contrary, activity of LTX-313 compound seemed to be increased by acquired resistance towards cisplatin as exhibited by a RI value of 0.49 for IGROV-1/CDDP cell line.

5.3. LTX-315

All thirty seven (37) human tumor cell lines tested were sensitive to LTX-315 compound with $IC_{50}$ values ranging from 1.18±0.25 µM to 7.16±0.99 µM for T-47D and SK-OV-3 cell lines, respectively.

Mean $IC_{50}$ value for LTX-315 compound obtained on the 37 tumor cell lines was 3.63±1.45 µM with a median value of 3.27 µM. Mean $IC_{50}$ value obtained for the normal cell line (HUV-EC-C) was higher than for any of the tumor cell lines.

Breast, hematological and lung cancer cell lines were the most sensitive to LTX-315 compound (median $IC_{50}$ values 2.45 µM (n=5), 2.60 µM (n=7) and 2.83 µM (n=3) for breast, hematological and lung cancer cell lines respectively) whereas liver cancer cell lines were the most resistant (median $IC_{50}$ value 5.86 µM, n=2).

Activity of LTX-315 compound seemed to be slightly decreased by acquired resistance towards doxorubicin as exhibited by the RI values of HL-60/ADR and MCF-7/mdr cell lines (1.45 and 1.12 for HL-60/ADR and MCF-7/mdr cell lines, respectively). On the contrary, activity of LTX-315 compound seemed to be increased by acquired resistance towards cisplatin as exhibited by a RI value of 0.50 for IGROV-1/CDDP cell line.

5.4. LTX-320

All thirty seven (37) human tumor cell lines tested were sensitive to LTX-320 compound with $IC_{50}$ values ranging from 3.46±0.22 µM to 16.64±3.15 µM for T-47D and Hep G2 cell lines, respectively.

Mean $IC_{50}$ value for LTX-320 compound obtained on the 37 tumor cell lines was 7.58±2.79 µM with a median value of 6.92 µM. Mean $IC_{50}$ value obtained for the normal cell line (HUV-EC-C) was higher than for any of the tumor cell lines.

Hematological, breast, kidney and brain cancer cell lines were the most sensitive to LTX-320 compound (median $IC_{50}$ values 6.04 µM (n=7), 6.60 µM (n=5), 6.60 µM (n=2) and 6.92 µM (n=3) for hematological, breast, kidney and brain cancer cell lines respectively) whereas liver cancer cell lines were the most resistant (median $IC_{50}$ value 11.46 µM, n=2).

Activity of LTX-320 compound seemed not to be modified by acquired resistance towards doxorubicin as exhibited by the RI values of HL-60/ADR and MCF-7/mdr cell lines (0.90 and 1.19 for HL-60/ADR and MCF-7/mdr cell lines, respectively). On the contrary, activity of LTX-320 compound seemed to be increased by acquired resistance towards cisplatin as exhibited by a RI value of 0.49 for IGROV-1/CDDP cell line.

5.5. LTX-329

All thirty seven (37) human tumor cell lines tested were sensitive to LTX-329 compound with $IC_{50}$ values ranging from 2.43±0.34 µM to 16.90±1.18 µM for T-47D and U-87 MG cell lines, respectively.

Mean $IC_{50}$ value for LTX-329 compound obtained on the 37 tumor cell lines was 8.17±3.20 µM with a median value of 7.89 µM. Mean $IC_{50}$ value obtained for the normal cell line (HUV-EC-C) was higher than for any of the tumor cell lines.

Breast and hematological cancer cell lines were the most sensitive to LTX-329 compound (median $IC_{50}$ values 4.92 µM (n=5) and 5.26 µM (n=7) for breast and hematological cancer cell lines respectively) whereas ovarian cancer cell lines were the most resistant (median $IC_{50}$ value 13.37 µM, n=4).

Activity of LTX-329 compound seemed not to be modified by acquired resistance towards doxorubicin as exhibited by the RI values of CCRF-CEM/VLB, HL-60/ADR and MCF-7/mdr cell lines (0.76, 0.80 and 1.07 for CCRF-CEM/VLB, HL-60/ADR and MCF-7/mdr cell lines, respectively). On the contrary, activity of LTX-329 compound seemed to be increased by acquired resistance towards cisplatin as exhibited by a RI value of 0.46 for IGROV-1/CDDP cell line.

5.6. General Comments

T-47D breast cancer cell line is the most sensitive cell line whatever the LTX compound tested.

Hematological cancer cell lines are the most sensitive histological type for all five compounds tested, liver and ovarian cancer cell lines being within the most resistant cell lines.

All five compounds tested exhibited highest activity on IGROV-1/CDDP cell line (resistant to cisplatin) than on parental IGROV-1 ovarian cancer cell line. Doxorubicin resistance seemed to slightly decrease activity of LTX compounds.

LTX-315 compound is the most potent compound from the five compounds tested.

6. Conclusions

All five compounds tested (i.e. LTX-302, LTX-313, LTX-315, LTX-320 and LTX-329) exhibited cytolytic activity against 37 human cancer cell lines tested with $IC_{50}$ values in micromolar to ten micromolar range.

LTX-315 compound is the most potent compound tested with $IC_{50}$ values between 1 and 5 micromolar on all 37 human cancer cell lines tested.

EXAMPLE 2

In vitro Cytotoxic Activity Study of 5 Test Compounds Against a Panel of 10 Lymphoma Cell Lines 1. Study Aim To determine the concentrations of five novel compounds to obtain a 50% inhibition of proliferation ($IC_{50}$) against a panel of 10 lymphoma cell lines.

2. Materials and Methods 2.1. Test Substances 2.1.1. Test Substances

Test substances, LTX-302, LTX-313, LTX-315, LTX-320 and LTX-329 (see Table 1) provided in powder form.

2.1.2. Positive Control

Triton X-100 was used as positive control and supplied by Oncodesign (Dijon, France) from Sigma (Saint Quentin Fallavier, France).

2.1.3. Drug vehicle and storage condition

Compounds were stored at 4° C. Powder was first dissolved in serum free culture medium (RPMI 1640, Lonza, Verviers, Belgium) and further diluted using serum-free culture medium to reach appropriate dilutions. Stock solution was not stored and was prepared fresh the day of experiment.

1% (final concentration) Triton X-100 was obtained by dilution using culture medium.

2.2. Tumor Cell Lines and Culture Conditions 2.2.1. Tumor Cell Lines

Cancer cell lines and culture media were purchased and provided by Oncodesign.

| N° | Cell lines | Origin | Source |
|---|---|---|---|
| | | BLOOD | |
| 1 | Daudi | Burkitt's lymphoma, B cells, peripheral blood | ATCC[a] |
| 2 | Hs 445 | Hodgkin's lymphoma, lymph node | ATCC |
| 3 | KARPAS-299 | Anaplastic large cell lymphoma, T cells, peripheral blood | DSMZ[b] |
| 4 | Mino | Mantle cell lymphoma, peripheral blood | ATCC |
| 5 | NAMALWA | Burkitt's lymphoma, B cells, peripheral blood | ATCC |
| 6 | Raji | Burkitt's lymphoma, B cells, peripheral blood | DSMZ |
| 7 | Ramos | Burkitt's lymphoma, B cells, peripheral blood | ATCC |
| 8 | SU-DHL-1 | Anaplastic large cell lymphoma, pleural effusion | DSMZ |
| 9 | Toledo | Non-Hodgkin's B cell lymphoma, peripheral blood | ATCC |
| 10 | U-937 | Lymphoma, histiocytic, macrophage differentiation, pleural effusion | ATCC |

[a]American Type Culture Collection, Manassas, Virginia, USA
[b]Deutsche Sammlung von Mikroorganismen und Zellkuturen Gmbh, Braunschweig, Germany 2.2.2. Culture Conditions Tumor cells were grown as suspensions at 37° C. in a humidified atmosphere (5% $CO_2$, 95% air). The culture medium for each cell line is described in the Table 3 below. For experimental use, cells were counted in a hemocytometer and their viability was assessed by 0.25% trypan blue exclusion.

TABLE 3

| Cell lines | Culture medium | FBS (%) | Glucose (g/l) | Glutamine (mM) | NaPyr (mM) | Hepes (mM) |
|---|---|---|---|---|---|---|
| Daudi | RPMI 1640 | 10 | — | 2 | 1 | 10 |
| Hs 445 | RPMI 1640 | 20 | 4.5 | 2 | 1 | 10 |
| KARPAS-299 | RPMI 1640 | 20 | — | 2 | — | — |
| Mino | RPMI 1640 | 15 | 4.5 | 2 | 1 | 10 |
| NAMALWA | RPMI 1640 | 10 | 2.5 | 2 | 1 | 10 |
| Raji | RPMI 1640 | 10 | — | 2 | 1 | 10 |
| Ramos | RPMI 1640 | 10 | — | 2 | 1 | 10 |
| SU-DHL-1 | RPMI 1640 | 10 | — | 2 | — | — |
| Toledo | RPMI 1640 | 15 | 4.5 | 2 | 1 | 10 |
| U-937 | RPMI 1640 | 10 | — | 2 | — | — |

Mycoplasma detection was performed using the MycoAlert® Mycoplasma Detection Kit (Lonza) in accordance with the manufacturer's instructions. All tested cells were found to be negative for mycoplasma contamination.

3. Experimental Design and Treatments 3.1. Cell Lines Amplification and Plating

Tumor cells were plated in 96-well flat-bottom microtitration plates (Nunc, Dutscher, Brumath, France) and incubated at 37° C. for 24 hours before treatment in 190 µl of drug-free and FBS-free culture medium.

Implantation densities for each cell lines are summarized in Table 4 below:

TABLE 4

| N° | Cell lines | Implantation densities (cells/well) |
|---|---|---|
| 1 | Daudi | 25,000 |
| 2 | Hs 445 | 25,000 |
| 3 | KARPAS-299 | 25,000 |
| 4 | Mino | 25,000 |
| 5 | NAMALWA | 15,000 |
| 6 | Raji | 20,000 |
| 7 | Ramos | 20,000 |
| 8 | SU-DHL-1 | 25,000 |
| 9 | Toledo | 25,000 |
| 10 | U-937 | 15,000 |

3.2. $IC_{50}$ Determination

Tumor cells were incubated for 4 hours with 10 concentrations of compounds in ¼ dilution step with a top dose of 400 µM (range $4 \times 10^{-4}$ to $4 \times 10^{-10}$ M), with 1% (final concentration) Triton X-100 as positive control and FBS-free culture medium as negative control. The cells (190 µl) were incubated in a 200 µl final volume of FBS-free culture medium containing test substances at 37° C. under 5% $CO_2$.

Three independent experiments were performed, each concentration being issued from quadruplicate. Control cells were treated with vehicle alone. At the end of treatments, the cytotoxic activity was evaluated by a MTS assay (see §3.3 below).

Dilutions of tested compound as well as distribution to plates containing cells were performed using a Sciclone ALH 3000 liquid handling system (Caliper Life Sciences S.A.). According to automate use, a single range of concentrations was tested whatever the cell lines to be tested. The range was not adapted for each cell line.

3.3. MTS Assay

The in vitro cytotoxic activity of the test substance was revealed by a MTS assay (Baltorp et al.) using a novel tetrazolium compound (MTS, 3-(4,5-dimethylthiazol-2-yl)-5-(3-carboxymethoxy phenyl)-2-(4-sulfophenyl)-2H-tetrazolium) and an electron coupling reagent named PMS (phenazine methosulfate). Like MTT, MTS is bioreduced by cells into a formazan product that is directly soluble in culture medium without processing, unlike MTT.

At the end of the cells treatment, 40 µl of a 0.22 µm filtered freshly combined solution of MTS (20 ml at 2 mg/ml, Ref G1111, Batch 235897, Exp March/2009, Promega, Charbonnières, France) and PMS (1 ml at 0.92 mg/ml, Ref P9625, Batch 065K0961, Sigma) in Dulbecco's Phosphate Buffered Saline (DPBS, Ref 17-513Q, Batch 6MB0152, Cambrex), were added in each well. Culture plates were incubated for 2 h at 37° C. Absorbency (OD) were measured at 490 nm in each well using VICTOR³™ 1420 multilabeled counter (Wallac, PerkinElmer, Courtaboeuf, France).

4. Data Presentation 4.1. $IC_{50}$ Data was Determined as in Example 1

5. Results 5.1. LTX-302

All ten (10) human lymphoma cell lines tested were sensitive to LTX-302 compound with $IC_{50}$ values ranging from 5.30±2.02 µM to 12.54±3.52 µM for U-937 and Raji cell lines, respectively.

Mean $IC_{50}$ value for LTX-302 compound obtained on 10 sensitive cell lines was 8.11±2.44 µM with a median value of 7.53 µM.

5.2. LTX-313

All ten (10) human lymphoma cell lines tested were sensitive to LTX-313 compound with $IC_{50}$ values ranging from 3.21±2.81 µM to 16.08±4.86 µM for Ramos and Raji cell lines, respectively.

Mean IC$_{50}$ value for LTX-313 compound obtained on 10 sensitive cell lines was 7.05±3.91 µM with a median value of 5.89 µM.

5.3. LTX-315

All ten (10) human lymphoma cell lines tested were sensitive to LTX-315 compound with IC$_{50}$ values ranging from 1.15±0.42 µM to 4.93±1.03 µM for U-937 and Raji cell lines, respectively.

Mean IC$_{50}$ value for LTX-315 compound obtained on 10 sensitive cell lines was 3.01±1.36 µM with a median value of 2.93 µM.

5.4. LTX-320

All ten (10) human lymphoma cell lines tested were sensitive to LTX-320 compound with IC$_{50}$ values ranging from 2.22±NA µM to 11.26±3.42 µM for Hs 445 and Raji cell lines, respectively.

Mean IC$_{50}$ value for LTX-320 compound obtained on 10 sensitive cell lines was 5.03±2.82 µM with a median value of 4.84 µM.

5.5. LTX-329

All ten (10) human lymphoma cell lines tested were sensitive to LTX-329 compound with IC$_{50}$ values ranging from 2.46±NA µM to 8.70±1.70 µM for Hs 445 and Raji cell lines, respectively.

Mean IC$_{50}$ value for LTX-329 compound obtained on 10 sensitive cell lines was 5.76±2.27 µM with a median value of 5.72

5.6. General Comments

KARPAS-299 and Raji cell lines are the most resistant cell lines whatever the LTX compound tested.

Hs 445, Ramos and U-937 cell lines are the most sensitive cell lines whatever the LTX compound tested.

LTX-315 compound is the most potent compound from the five compounds tested.

6. Conclusions

All five compounds tested (i.e. LTX-302, LTX-313, LTX-315, LTX-320 and LTX-329) exhibited cytolytic activity against the 10 human lymphoma cell lines tested with IC$_{50}$ values in micromolar range.

LTX-315 compound is the most potent compound tested with IC$_{50}$ values between 1 and 5 micromolar on all 10 human lymphoma cell lines tested.

EXAMPLE 3

Hemolytic Activity In vitro

Principle of Test

The hemolytic activity of the peptide LTX-315 against human red blood cells was measured.

Materials and Methods

Freshly collected human blood was centrifuged at 1500 rpm for 10 minutes in order to isolate the red blood cells. The red blood cells (RBC) were washed three times with PBS [35 mM phosphate buffer with 150 mM NaCl, pH 7.4] by centrifugation at 1500 rpm for 10 minutes, and adjusted to 10% hematocrit with PBS. LTX-315 solutions were added to give a final concentration range of the peptide from 1200 µg/ml to 1 µg/ml and an RBC concentration of 1%. The resulting suspension was incubated with agitation for one hour at 37° C. After incubation the suspension was centrifuged at 4000 rpm for 5 minutes, and the released haemoglobin were monitored by measuring the absorbance of the supernatant at 405 nm. PBS was used as negative control and assumed to cause no hemolysis. 0.1% Triton was used as positive control and assumed to cause complete hemolysis.

Test Substance: LTX-315

Reference substances: PBS (negative control) and Triton X-100 (positive control) Components of reaction mixtures: LTX-315, 10% Triton X-100, PBS and RBC (10% hematocrit)

| Concentration | PBS (µl) | RBC (µl) | LTX-315/Triton X-100 (µl) |
|---|---|---|---|
| Neg. Control | 630 | 70 | — |
| Pos. Control | 623 | 70 | 7 |
| 1200 | 150 | 50 | 300 (2 mg/ml stock) |
| 1000 | 200 | 50 | 250 (2 mg/ml stock) |
| 500 | 325 | 50 | 125 (2 mg/ml stock) |
| 100 | 595 | 70 | 35 (2 mg/ml stock) |
| 50 | 612.5 | 70 | 17.5 (2 mg/ml stock) |
| 10 | 560 | 70 | 70 (0.1 mg/ml stock) |
| 1 | 623 | 70 | 7 (0.1 mg/ml stock) |

Method of Evaluation:

Released haemoglobin was monitored by measuring the absorbance of the supernatant at 405 nm, and percent hemolysis was calculated by the equation:

$$\text{hemolysis} = [(A_{405}LTX\text{-}315 - A_{405}PBS)/(A_{405}0.1\% \text{Triton } X\text{-}100 - A_{405}PBS)] \times 100$$

LTX-315 concentration corresponding to 50% hemolysis (EC$_{50}$) was determined from a dose-response curve.

Results

Mean value of five different experiments with standard deviation are presented below. The data is also represented in FIG. 1. FIG. 1 shows that LTX-315 has a mean value of EC$_{50}$ higher than 1200 µg/ml (833 µM).

| LTX-315 Concentration (µg/ml) | Mean cell death (%) | Standard Deviation | Number of parallels |
|---|---|---|---|
| 1200 | 37.7 | 8.1445 | 3 |
| 1000 | 38.2 | 9.5760 | 5 |
| 500 | 20.4 | 7.8613 | 5 |
| 100 | 3.6 | 1.1402 | 5 |
| 50 | 1.6 | 0.5477 | 5 |
| 10 | 0.6 | 0.8944 | 5 |
| 1 | 0.0 | 0.000 | 5 |

EXAMPLE 4

Pharmacodynamic Effects Relative to Murine A20 B-Cell Lymphoma Tumours in Mice

Principle of Test

The aim of the study was to investigate the effect of LTX-315 at different dose levels on a murine A20 B-cell lymphoma in mice.

Materials and Methods

The administration took place by intratumoral injection of LTX-315 dissolved in sterile saline.

Female mice were inoculated subcutaneously in the abdomen with 5 million murine A20 cells (ATCC, LGC Promochem AB, Middlesex, England) in a volume of 50 µl. The mice were divided into four groups (see Table 5 below for details). The intratumoral treatment was initiated when the tumours had reached the desired size of approximately 5 mm in diameter (minimum of 20 mm$^2$).

Three dose levels of LTX-315, 1 mg (Group 1), 0.5 mg (Group 2) and 0.25 mg (Group 3) per injection, were investigated. The volume was 50 µl for all injections. LTX-315 was dissolved in sterile 0.9% NaCl water solution. This vehicle was used as control (Group 4). All four groups received three injections.

The mice were monitored during the study by measuring the tumours and weighing the animals regularly. The mice were followed until the maximum tumour burden of 125 mm² was reached, or until serious adverse events occurred (i.e. wound formation upon repeated treatments during the follow up period), then the mice were sacrificed. A caliper was used for tumour size measurements and weighing and physical examination were used as health control.

Animals: Specific pathogen-free female Balb/c mice, 6-8 weeks old, supplied form Harlan (England, UK)

Conditioning of animals: Animals were kept on standard laboratory chow and water.

Mean body weight, dose, route and treatment schedule is given in Table 5 below.

TABLE 5

| Group | Number of animals | Initial body weight (g; mean ± SE) | Treatment | Dose | Route | Schedule (Day*) |
|---|---|---|---|---|---|---|
| 1 | 7 | 20.36 ± 0.56 | Once daily | 1 mg in 50 μl (20 mg/ml) | Intra tumour | 1, 2, 3 |
| 2 | 7 | 19.96 ± 0.38 | Once daily | 0.5 mg in 50 μl (10 mg/ml) | Intra tumour | 1, 2, 3 |
| 3 | 9 | 20.11 ± 0.33 | Once daily | 0.25 mg in 50 μl (5 mg/ml) | Intra tumour | 1, 2, 3 |
| 4 | 7 | 19.73 ± 0.40 | Once daily | 50 μl 0.9% NaCl in H₂0 | Intra tumour | 1, 2, 3 |

*Day 1 is first day of treatment

Results:

The anti-tumour effect of the various treatments is presented as mean tumour size in Table 6 below.

TABLE 6

| Treatment | Mean tumour size (mm²) at day 1* | Mean tumour size (mm²) on day 4 | Mean tumour size (mm²) on day 9 | Mean tumour size (mm²) on day 14 |
|---|---|---|---|---|
| Group 1 | 25.82 ± 0.80 | 0 | 3.70 ± 2.40 | 12.43 ± 7.87 |
| Group 2 | 22.03 ± 0.63 | 0 | 11.41 ± 4.69 | 61.08 ± 23.84 |
| Group 3 | 21.25 ± 0.64 | 20.60 ± 5.71 | 68.49 ± 12.74 | 69.42 ± 17.70 |
| Group 4 | 22.79 ± 0.68 | 45.51 ± 5.27 | 57.79 ± 4.39 | 84.70 ± 7.35 |

*Tumour size prior to start of treatment at first day of treatment

The degree of tumour response in the different treatment groups is summarized in Table 7 below.

TABLE 7

| Animal Group | Tumour Response | | | Relapse of Tumour | Free of Tumour at end of Follow-Up |
|---|---|---|---|---|---|
| | no response | partial response | complete response | | |
| 1 | 0 | 42.8% (3/7) | 57.2% (4/7) | 25% | 42.8% (3/7) |
| 2 | 0 | 71.42% | 28.57% (2/7) | 0% (0/2) | 28.57% (2/7) |
| 3 | 77.77% | 22.22% | 0% (0/9) | NA | 0 |
| 4 | 100% | NA | NA | NA | NA |

Discussion/Conclusions

In Group 3, receiving the lowest LTX-315 dose (0.25 mg/dose), a small inhibitory effect is observed during the first days. In Group 1 and Group 2, receiving LTX-315 doses of 1.0 mg/dose and 0.5 mg/dose respectively, all animals showed partial or complete tumour response. It was found that the anti-tumour activity resulted in a complete tumour response in 3 of 7 treated mice for the Group receiving the optimal dose (Group 1).

Generally stronger necrosis and more wound formation were observed in Group 1 compared to the other two groups. Except from the wound formation no other adverse events or toxic effects were observed in either of the groups of animals.

Both 1 mg and 0.5 mg of LTX-315 demonstrated a strong and rapid anti tumour effect in the first period of the study. However, as the study progresses more animals in Group 2 relapses than in Group 1.

EXAMPLE 5

The Effect of LTX-315 on Murine CT26WT Colon Carcinoma Tumours in Mice

Materials and Methods

The administration takes place by intra-tumoural injection of LTX-315 dissolved in sterile saline (0.9% NaCl in sterile water).

Each of a total of 40 female mice was inoculated with five million murine CT26WT cells (ATCC, LGC Promochem AB, Boras, Sweden) subcutaneously on the abdomen surface in a volume of 50 μl. The mice were divided into five groups, 8 mice in each group. When the tumours reached the desired size of 20 mm² the treatment by intra tumoural injection was initiated. Group one was treated solely on day 1, Group two on day 1 and 2, Group three on day 1 and 3 and Group four on day 1, 2 and 3. All daily treatments were one single injection of 1.0 mg LTX-315 dissolved in 50 μl (20 mg/ml). Group five was treated with the 50 μl of vehicle for LTX-315 (Group 5).

The mice were monitored during the study by measuring the tumours (digital caliper) and weighing the animals regularly. The mice were followed until the maximum tumour burden of 125 mm² was reached, or until serious adverse events occurred (i.e. wound formation due to repeated injections), then the mice were sacrificed. Weighing and physical examination were used as health controls.

Animals: Specific pathogen-free female Balb/c mice, 6-8 weeks old, supplied form Harlan (England, UK)

Conditioning of animals: Standard animal facility conditions.

Mean body weight, dose, route and treatment schedule is given in Table 8 below.

TABLE 8

| Group | Number of animals | Initial body weight (g; mean ± SE) | Treatment | Dose | Route | Schedule (Day*) |
|---|---|---|---|---|---|---|
| 1 | 8 | 19.00 ± 1.087 | Once daily | 1 mg in 50 μl (20 mg/ml) | Intra tumour | 1 |
| 2 | 8 | 19.56 ± 1.087 | Once daily | 1 mg in 50 μl (20 mg/ml) | Intra tumour | 1, 2 |
| 3 | 8 | 19.41 ± 0.8999 | Once daily | 1 mg in 50 μl (20 mg/ml) | Intra tumour | 1, 3 |

TABLE 8-continued

| Group | Number of animals | Initial body weight (g; mean ± SE) | Treatment | Dose | Route | Schedule (Day*) |
|---|---|---|---|---|---|---|
| 4 | 8 | 19.00 ± 0.9396 | Once daily | 1 mg in 50 μl (20 mg/ml) | Intra tumour | 1, 2, 3 |
| 5 (control) | 8 | 18.71 ± 0.7868 | Once daily | 50 μl 0.9% NaCl in $H_2O$ | Intra tumour | 1, 2, 3 |

*Day 1 is first day of treatment

Results

The anti-tumour effect of the various treatments is presented as mean tumour size in Table 9 below.

TABLE 9

| Treatment | Mean tumour size ($mm^2$) at day 1* | Mean tumour size ($mm^2$) on day 6 | Mean tumour size ($mm^2$) on day 10 | Mean tumour size ($mm^2$) on day 17 |
|---|---|---|---|---|
| Group 1 | 22.69 ± 0.4070 | 4.343 ± 2.295 | 7.171 ± 4.035 | 3.712 ± 3.712 |
| Group 2 | 22.90 ± 1.155 | 1.458 ± 1.458 | 5.058 ± 4.014 | 6.644 ± 3.430 |
| Group 3 | 21.43 ± 1.141 | 2.983 ± 2.983 | 10.85 ± 7.553 | 0.00 ± 0.00 |
| Group 4 | 24.09 ± 1.653 | 0.00 ± 0.00 | 0.00 ± 0.00 | 1.308 ± 1.308 |
| Group 5 | 21.39 ± 1.683 | 33.77 ± 3.168 | 48.37 ± 7.035 | 40.64 ± 19.77 |

*Tumour size prior to start of treatment at first day of treatment

Complete tumour response was observed in the vast majority of all animals treated with LTX-315. The degree of tumour response in the different treatment groups is summarized in Table 10 below.

TABLE 10

| Animal Group | Tumour Response | | | Relapse of Tumour | Free of Tumour at end of Follow-Up |
|---|---|---|---|---|---|
| | no response | partial response | complete response | | |
| 1 | 0 | 27.5% | 62.5% | 20% (1/5) | 50% (4/8) |
| 2 | 0 | 12.5% | 87.5% | 71% (5/7) | 25% (2/8) |
| 3 | 12.5% | 0 | 87.5% | 29% (2/7) | 62.5% (5/8) |
| 4 | 0 | 0 | 100% (8/8) | 37.5% | 62.5% (5/8) |
| 5 | 100% (8/8) | NA | NA | NA | NA |

Discussion/Conclusions

The treatment was started when the tumours had reached the desired size of a minimum of 20 $mm^2$ and animals were sacrificed when the tumours reached the maximum tumour burden of 125 $mm^2$.

End of study was defined as day 17 when six out of eight control animals (Group 5) were sacrificed.

All LTX-315 treatment regimes resulted in a strong anti CT26WT-tumour effect.

Totally 27 of the 32 treated animals were observed with a complete tumour response and four with a partial response. Only one animal (in Group 3) did not have a response to the treatment. The results presented show that all four treated groups have very similar overall tumour response, the data also indicate that the degree of relapse of tumour was higher in Group 2 than in Group 1, 3 and 4. In addition fewer animals were observed to be free of tumour at end of follow-up in Group 2 (FIG. 2).

Necrosis and complete tumour response was observed in all the treated groups. In Group 1 four out of eight animals, in Group 2 two out of eight animals, in Group 3 five out of eight animals, and in Group 4 five out of eight animals showed complete tumour response. At this stage the tumour was completely necrotic and a wound crust formed at the location of the tumour.

Necrosis at the tumour site was seen in all treatment groups. Generally, animals in Group 2, 3 and 4 showed more necrosis, wound and crust formation than the animals in Group 1 that were given only one injection of LTX-315. Group 4 animals, which were given three injections, showed the most necrosis, wound and crust formation. The difference in necrosis between Group 1 and Group 4 was quite large but the animals given the highest number of treatments seemed to cope well. No toxic or other adverse effects besides local necrotic tissue and wound formation were observed in either of the treated groups of animals.

All four treatment regimes of LTX-315 tested demonstrated a strong anti tumour effect against murine CT26WT tumours.

The amount of necrosis, wound and crust formation was proportional to the number of LTX-315 treatments given.

EXAMPLE 6

LTX-315 Activity Against Sensitive and Multidrug-Resistant Cancer Cells and Normal Human Cells

| Cell line | Drug susceptibility | Origin | $IC_{50}$ μM |
|---|---|---|---|
| HL-60 | Sensitive | Acute promyelocytic leukemia | 2.07 |
| HL-60/ADR | Resistant | Acute promyelocytic leukemia | 3.01 |
| MCF-7 | Sensitive | Breast carcinoma | 1.94 |
| MCF-7/mdr | Resistant | Breast carcinoma | 1.96 |
| IGROV-1 | Sensitive | Ovary carcinoma | 6.37 |
| IGROV-1/CDDP | Resistant | Ovary carcinoma | 3.19 |
| K-562 | Sensitive | Chronic myeloid leukemia | 3.27 |
| K5627/Gleevec | Resistant | Chronic myeloid leukemia | 2.98 |
| HUV-EC-C | — | Normal endothelial cells | 23 |
| RBC | — | Red blood cells | 833 |

The above data shows the broad spectrum of activity of LTX-315 against various cancer cell lines and, significantly, a much weaker cytotoxic effect on normal human cells.

EXAMPLE 7

Re-challenge with Murine A20 B-Cell Lymphoma and Murine CT26WT Colon Carcinoma Cells in Mice with Complete Tumour Regression This study sought to investigate the effects of tumour growth in animals that had previously shown complete tumour regression following treatment with LTX-315.

Methods: Female Balb-c mice (n=4), previously treated with LTX-315, 1 mg) or (n=9); previously treated with LTX-315 0.5 or 1 mg) were re-inoculated (s.c. in the abdominal area) with either murine A20 B cell lymphoma cells or CT26WT colon carcinoma cells (5 million) respectively 6 weeks following initial treatment with LTX-315. Tumour growth was monitored for up to 36 days following re-inoculation.

Significant inhibition (P<0.006) of tumour growth was observed in all 4 mice treated previously with LTX-315 (1 mg) in study R315-03 compared with control animals (FIG. 2) and while relapse was seen in 1 animal, 3 weeks later, complete tumour regression was observed in the other 3 mice (FIG. 3).

In 9 mice previously treated with LTX-315 (0.5 or 1 mg) inhibition (P<0.01) of tumour growth was observed in comparison with control animals (FIG. 3). The sudden drop in tumour size in FIG. 20, after Day 18, is explained by the death of 6 animals bearing large tumours. Inhibition was observed in 7 mice and complete regression in 2 of the animals (FIG. 5).

Taken together these data suggest that complete tumour regression following initial treatment of solid murine tumours (murine A20 B cell lymphoma or CT26WT colon carcinoma) with LTX-315 resulted in a form of endogenous long-term protection against growth of the same tumours following re-inoculation. Inhibition of tumour growth was more pronounced in animals bearing A20 B cell lymphoma tumours when compared with animals bearing CT26WT colon tumours.

EXAMPLE 8

Immunological effects of LTX-315 in a murine A20 B-cell lymphoma model. An in vivo adoptive spleen cell transfer pilot study.

This study was undertaken to investigate whether the long-term protection against growth of the same tumours following re-inoculation in animals observed in study R315-33 could be passively transferred to naive recipients via spleen cells taken from LTX-315-treated donor animals.

Ten female Balb/c mice (n=32) were each inoculated with A20 cells (5 million in 50 µL s.c.) on the abdominal surface. Once tumours had reached 20 mm$^2$ they were injected with LTX-315 (1 mg) injected intratumorally, once daily for 3 days, in a volume of 50 µL. Tumour size (mm$^2$) and body weight were subsequently monitored and a further injection of LTX-315 was given if any tumour re-growth was observed. Subsequently, mice showing complete tumour regression were sacrificed and used as donors for transfer of splenocytes while naive donor mice were used as controls. Spleens from donor mice were excised and cells isolated. Naive receiver mice were irradiated and divided into 2 groups. Group 1 received isolated splenocytes from cured mice, whereas group 2 received isolated splenocytes from naive mice. Freshly prepared cells were injected (20×106 per 100 µl) via the tail vein. Twenty four hours later receiver mice were inoculated with 5 million murine A20 B-cell lymphoma cells on the abdominal surface as described above. Tumour size and body weight were monitored until the maximum tumour burden of ~125 mm$^2$ was reached, or a serious adverse events occurred (i.e. wound formation due to tumour tissue necrosis) at which point mice were sacrificed.

Inhibition of tumour growth was observed in irradiated mice that received splenocytes isolated from animals that had shown complete tumour regression following treatment with LTX-315 when compared with control animals that received splenocytes from naive donors (FIG. 6). It was also noted that there was a difference in the colour and texture of the tumours in recipients of splenocytes from LTX-315-treated mice suggesting an immediate inflammatory response.

Based on these observations, the data provides evidence for an adaptive immune response in the animals that received splenocytes from animals that previously showed complete regression of A20-B lymphoma tumours following treatment with LTX-315. This data suggests that treatment with LTX-315 may confer long term protection against specific tumours by eliciting an immune response.

EXAMPLE 9

The objective of the study was to investigate the anti-cancer effect of prophylactic vaccination with A20 lymphoma cells lysed by 10 mg/ml LTX-315:
  (i) alone; and
  (ii) in combination with 20 mg/ml LTX-315 injected at the vaccination site prior to the vaccine.

In total, two different treatment regimens were used.

Administration was by subcutaneous injection of LTX-315 dissolved in growth media containing A20 lymphoma cells. The cell-LTX-315 "cocktail" was left for 30 min prior to injection in order to assure complete lysis of the cancer cells.

Group 1 ("vaccine") mice were injected subcutaneously on the abdomen surface with 50 µl of a "cocktail" of ten million murine A20 cells (ATCC, LGC Promochem AB, Boras, Sweden) and 10 mg/ml LTX-315 ("A20 lysate"). Group 2 ("vaccine+adjuvant") mice were treated as per Group 1, but in addition were given 25 µl of 20 mg/ml LTX-315 subcutaneously at the site of vaccination 5 minutes prior to the A20 lysate injection. Group 3 ("control") mice received no treatment.

Six weeks after the treatment, all mice were inoculated with 5 million viable A20 B-cell lymphoma cells subcutaneously on the abdomen surface in a volume of 50 µl.

The mice were monitored during the study by measuring the tumour size and weighing the animals regularly. The mice were followed until the maximum tumour burden of ~130 mm$^2$ was reached, at which point the mice were sacrificed.

Materials and Methods

Animals: Specific pathogen-free female Balb/c mice, 6-8 weeks old, supplied from Harlan Laboratories (England, UK)

Conditioning of animals: Standard animal facility conditions at the University of Tromso.

Test substance: Murine A20 cells lysed by LTX-315 (Lot 1013687), and LTX-315 (Lot 1013687) alone Test substance preparation: 10×10$^6$ A20 cells were added to a 50µl 10 mg/ml LTX-315/vehicle ("A20 lysate"). The test substance was ready for use 30 minutes after mixing. LTX-315 alone was dissolved in 0.9% NaCl in sterile H$_2$O Vehicle: RPMI-1640 w/2 mM L-glutamine or 0.9% NaCl in sterile H$_2$O Reference substances: Not applicable Treatment of controls: Not applicable Method of evaluation: Tumour size measurements and health control by weighing and examination Additional data regarding method: A digital caliper was used for tumour size measurements and weighing and physical examination were used as health control Mean body weight, dose, route and treatment schedule are shown in Table 11 (below).

TABLE 11

| Group | No of animals | Initial body weight (g; mean ± SE) | Treatment | Cell numbers and dose | Route |
|---|---|---|---|---|---|
| 1 | 8 | 17.31 ± 0.3815 | Once | 10 × 10⁶ A20 cells in 50 μl LTX-315 (10 mg/ml) | Subcutaneous |
| 2 | 8 | 17.14 ± 0.4633 | Once | 0.25 μl LTX-315 (20 mg/ml) + 10 × 10⁶ A20 cells in 50 μl LTX-315 (10 mg/ml) | Subcutaneous |
| 3 | 7 | 17.29 ± 0.3020 | Not treated | Not applicable | Not applicable |

Results:

The anti cancer effect of the various treatments is presented as mean tumour size in Table 12 below and a graphical presentation of the data is provided in FIG. 7. In Table 12, Day 1 was the day of inoculation of viable A20 cells six weeks post-vaccination.

TABLE 12

| Treatment | Mean tumour size (mm²) at day 4 | Mean tumour size (mm²) on day 11 | Mean tumour size (mm²) on day 16 | Mean tumour size (mm²) on day 21 |
|---|---|---|---|---|
| Group 1 | 9.515 ± 1.528 | 20.44 ± 6.191 | 36.21 ± 10.30 | 55.89 ± 15.27 |
| Group 2 | 7.315 ± 2.231 | 17.13 ± 5.078 | 29.13 ± 7.903 | 47.16 ± 13.54 |
| Group 3 | 10.25 ± 3.100 | 34.49 ± 8.298 | 56.04 ± 8.339 | 82.89 ± 14.06 |

Discussion/Conclusions:

The inoculation of viable A20 B-cell lymphoma cells was accomplished 6 weeks after the treatment was given (day 1) and the animals were sacrificed when the tumours reached the maximum allowed tumour burden of ~130 mm².

The results show that the tumours developed more slowly in both LTX-315/A20-lysate treatment Groups as compared to the control Group. The median survival of Group 1 was 28 days, 33 days for Group 2, and 25 days for the control group (Group 3). Increase in median survival was 12% for Group 1 and 35% for Group 2 as compared to the control group (Group 3).

The data indicate a prolonged survival of the treated groups compared to the untreated control group. On day 34, when the last animal in the control group was sacrificed, 50% of the animals in Group 2 were still alive while 37.5% of the animals in Group 1 were still alive. End of study was defined as day 60. At this time-point, a total of 3 of the 16 treated animals had a complete regression of an initially developing tumour and were tumour free. At the end of the study 25% of animals from Group 1, and 12.5% of animals from Group 2 were observed to be tumour free.

Macroscopically there were morphological differences between the treated groups (Group 1 and 2) compared to the non-treated control group (Group 3). The developing tumours in the two treatment groups were observed to be whiter and harder than the tumours observed in the control group. This finding together with the slower growth rate of the tumours indicates that an anti-A20 cell immune response was induced by the vaccination with the cocktail of LTX-315 and lysed A20 cells.

Hence, LTX-315 may have a dual use by lysing the tumour cells and inducing release of danger signals from normal cells at the injection site.

It will be appreciated that it is not intended to limit the present invention to the above specific embodiments only, numerous embodiments, modifications and improvements being readily apparent to one of ordinary skill in the art without departing from the scope of the appended claims.

The invention claimed is:

1. A compound having the formula of SEQ ID NO: 23 (LTX-315), or a salt, ester or amide thereof.

2. A composition comprising the compound as claimed in claim 1, in combination with a pharmaceutically acceptable carrier, diluent or excipient.

3. A composition comprising the compound as claimed in claim 1 in combination with at least one other therapeutic ingredient.

4. A composition comprising a compound having the formula of SEQ ID NO: 23 (LTX-315), or a salt, ester or amide thereof in combination with at least one vaccine.

5. A pharmaceutical pack comprising:
   (i) at least one vaccine; and
   (ii) a compound having the formula of SEQ ID NO: 23 (LTX-315), or a salt, ester or amide thereof.

6. A method of treatment of a tumor, comprising the step of administering a pharmaceutically effective amount of the compound as claimed in claim 1 to a patient in need of such treatment.

7. A method of vaccination, comprising the step of administering a pharmaceutically effective amount of the compound as claimed in claim 1 and a vaccine to a patient.

8. The composition as claimed in claim 4 wherein said vaccine is either a tumor lysate or an anti-cancer vaccine containing at least one protein and/or peptide with amino acid sequences corresponding to immunogenic sequence(s) from tumor associated antigen(s).

9. The composition as claimed in claim 4 wherein said vaccine is an anti-virus vaccine containing at least one protein and/or peptide with amino acid sequence(s) corresponding to immunogenic sequences from viral protein(s).

10. The pharmaceutical pack as claimed in claim 5 wherein said vaccine is either a tumor lysate or an anti-cancer vaccine containing at least one protein and/or peptide with amino acid sequences corresponding to immunogenic sequence(s) from tumor associated antigen(s).

11. The pharmaceutical pack as claimed in claim 5 wherein said vaccine is an anti-virus vaccine containing at least one protein and/or peptide with amino acid sequence(s) corresponding to immunogenic sequences from viral protein(s).

12. The method of vaccination as claimed in claim 7 wherein said vaccine is either a tumor lysate or an anti-cancer vaccine containing at least one protein and/or peptide with amino acid sequences corresponding to immunogenic sequence(s) from tumor associated antigen(s).

13. The method of vaccination as claimed in claim 7 wherein said vaccine is an anti-virus vaccine containing at least one protein and/or peptide with amino acid sequence(s) corresponding to immunogenic sequences from viral protein(s).

* * * * *